United States Patent
Dayton et al.

(10) Patent No.: US 8,460,905 B2
(45) Date of Patent: Jun. 11, 2013

(54) ENZYMATIC DEGUMMING UTILIZING A MIXTURE OF PLA AND PLC PHOSPHOLIPASES WITH REDUCED REACTION TIME

(75) Inventors: Christopher L. G. Dayton, Mount Kisco, NY (US); Erin Marie Rosswurm, Columbus, IN (US); Flavio da Silva Galhardo, Manteno, IL (US)

(73) Assignee: Bunge Oils, Inc., St. Louis, MO (US)

( * ) Notice: Subject to any disclaimer, the term of this patent is extended or adjusted under 35 U.S.C. 154(b) by 1408 days.

(21) Appl. No.: 11/853,339

(22) Filed: Sep. 11, 2007

(65) Prior Publication Data
US 2009/0069587 A1 Mar. 12, 2009

(51) Int. Cl.
| | |
|---|---|
| C12P 7/64 | (2006.01) |
| C12P 7/00 | (2006.01) |
| C12N 9/20 | (2006.01) |
| A61K 36/48 | (2006.01) |
| C12P 1/00 | (2006.01) |
| C12N 9/00 | (2006.01) |
| C12N 9/14 | (2006.01) |
| C02F 1/00 | (2006.01) |
| C11B 13/00 | (2006.01) |
| C11B 3/02 | (2006.01) |

(52) U.S. Cl.
USPC ......... 435/134; 435/41; 435/183; 435/195; 435/198; 210/632; 554/175; 424/757

(58) Field of Classification Search
None
See application file for complete search history.

(56) References Cited

U.S. PATENT DOCUMENTS
| | | | |
|---|---|---|---|
| 5,204,002 A | 4/1993 | Belfort et al. | |
| 5,264,367 A | 11/1993 | Aalrust et al. | |
| 5,266,207 A | 11/1993 | Boye et al. | |
| 5,342,521 A | 8/1994 | Bardot et al. | |
| 5,532,163 A | 7/1996 | Yagi et al. | |
| 5,558,781 A | 9/1996 | Buchold et al. | |

(Continued)

FOREIGN PATENT DOCUMENTS
| | | |
|---|---|---|
| EP | 654527 | 11/1994 |
| JP | 63279751 | 11/1988 |

(Continued)

OTHER PUBLICATIONS

Dahlke, K. and Eichelsbacher, M. "EnzyMax® and ALCON® —Lurgi's route to Physical Refining", AOCS Press, Champiagn, IL , 1998, pp. 53-59.*

(Continued)

*Primary Examiner* — Chris R Tate
*Assistant Examiner* — Aaron J Kosar
(74) *Attorney, Agent, or Firm* — Jones Day

(57) ABSTRACT

A method for degumming an oil composition comprises the steps of (a) providing an oil composition containing a quantity of phospholipids, (b) contacting said oil composition simultaneously with one or more phospholipase A enzymes and one or more phospholipase C enzymes, under conditions sufficient for the enzymes to react with the phospholipids to create phospholipid reaction products, and (c) separating the phospholipids reaction products from the oil composition, the remaining oil composition after the separation being a degummed oil composition, whereby during step (b) the reaction of said one or more phospholipase A enzymes proceeds at a faster rate than it would in the absence of said one or more phospholipase C enzymes, and wherein the reaction of step (b) continues for a duration of less than about one hour.

19 Claims, 5 Drawing Sheets

PHOSPHOLIPID

TRIACYLGLYCEROL $R_\#$ = FATTY ACID CHAINS
X = FUNCTIONAL GROUP

U.S. PATENT DOCUMENTS

| | | |
|---|---|---|
| 6,001,626 A | 12/1999 | Kosugi et al. |
| 6,001,640 A | 12/1999 | Loeffler et al. |
| 6,103,505 A | 8/2000 | Clausen et al. |
| 6,127,137 A | 10/2000 | Hasida et al. |
| 6,140,094 A | 10/2000 | Loffler et al. |
| 6,143,545 A | 11/2000 | Clausen et al. |
| 6,146,869 A | 11/2000 | Harris et al. |
| 6,441,208 B2 | 8/2002 | Bijl et al. |
| 6,475,758 B2 | 11/2002 | Reany |
| 6,489,154 B1 | 12/2002 | Berka et al. |
| 6,506,588 B2 | 1/2003 | Tsutsumi et al. |
| 6,509,182 B2 | 1/2003 | Tsutsumi |
| 6,511,837 B2 | 1/2003 | Tsutsumi |
| 6,514,739 B1 | 2/2003 | Udagawa et al. |
| 6,540,915 B2 | 4/2003 | Patil |
| 6,548,633 B1 | 4/2003 | Edward et al. |
| 6,645,749 B2 | 11/2003 | Vind |
| 6,682,922 B2 | 1/2004 | Berka et al. |
| 6,695,967 B2 | 2/2004 | Bishop et al. |
| 6,727,373 B2 | 4/2004 | Bijl et al. |
| 6,733,814 B2 | 5/2004 | 't Hooft et al. |
| 6,759,225 B2 | 7/2004 | Udagawa et al. |
| 6,833,073 B2 | 12/2004 | Agarwal |
| 6,887,380 B2 | 5/2005 | Lee et al. |
| 6,887,408 B2 | 5/2005 | Yuan |
| 6,913,786 B2 | 7/2005 | Proulx et al. |
| 7,063,792 B2 | 6/2006 | Ozanne et al. |
| 7,091,003 B1 | 8/2006 | Harris et al. |
| 7,094,346 B2 | 8/2006 | Osenar et al. |
| 7,148,032 B2 | 12/2006 | Stringer et al. |
| 7,172,742 B2 | 2/2007 | Feng et al. |
| 7,186,344 B2 | 3/2007 | Hughes |
| 7,713,727 B2 * | 5/2010 | Dayton et al. ............... 435/267 |
| 2002/0161066 A1 | 10/2002 | Remigy et al. |
| 2003/0000874 A1 | 1/2003 | Proulx et al. |
| 2003/0075506 A1 | 4/2003 | Tudhope |
| 2003/0090028 A1 | 5/2003 | Blase et al. |
| 2003/0121841 A1 | 7/2003 | Harttig et al. |
| 2003/0135971 A1 | 7/2003 | Liberman et al. |
| 2003/0144165 A1 | 7/2003 | Roggen |
| 2003/0186405 A1 | 10/2003 | Lee et al. |
| 2003/0203377 A1 | 10/2003 | Milne Edwards et al. |
| 2004/0005399 A1 | 1/2004 | Chakrabarti et al. |
| 2004/0005604 A1 | 1/2004 | Gramatikova et al. |
| 2004/0011723 A1 | 1/2004 | Bradford et al. |
| 2004/0101928 A1 | 5/2004 | Tsutsumi et al. |
| 2004/0110939 A1 | 6/2004 | Dumas Milne Edwards et al. |
| 2004/0159603 A1 | 8/2004 | Boulnois et al. |
| 2004/0179984 A1 | 9/2004 | Nagaraj et al. |
| 2004/0211726 A1 | 10/2004 | Baig et al. |
| 2004/0222148 A1 | 11/2004 | Yuan |
| 2004/0238439 A1 | 12/2004 | Oglesby |
| 2005/0009068 A1 | 1/2005 | Udagawa et al. |
| 2005/0059130 A1 | 3/2005 | Bojsen et al. |
| 2005/0061744 A1 | 3/2005 | Kearney et al. |
| 2005/0067340 A1 | 3/2005 | Broens et al. |
| 2005/0087491 A1 | 4/2005 | Hennige et al. |
| 2005/0106665 A9 | 5/2005 | Stringer et al. |
| 2005/0108789 A1 | 5/2005 | Gramatikova et al. |
| 2005/0118697 A1 | 6/2005 | Budolfsen et al. |
| 2005/0173330 A1 | 8/2005 | Osenar et al. |
| 2005/0284814 A1 | 12/2005 | Mairal et al. |
| 2006/0009633 A9 | 1/2006 | Dumas Milne Edwards et al. |
| 2006/0011544 A1 | 1/2006 | Sharma et al. |
| 2006/0030012 A1 | 2/2006 | Kellens et al. |
| 2006/0086654 A1 | 4/2006 | Voigt et al. |
| 2007/0134777 A1 * | 6/2007 | Dayton et al. ............... 435/134 |
| 2008/0182322 A1 * | 7/2008 | Dayton et al. ............... 435/271 |
| 2011/0136187 A1 | 6/2011 | Soe et al. |

FOREIGN PATENT DOCUMENTS

| | | |
|---|---|---|
| JP | 02-153997 | 6/1990 |
| JP | 06306386 | 11/1994 |
| JP | 11-131089 | 5/1999 |
| JP | 11228986 | 8/1999 |
| JP | 2005328781 | 12/2005 |
| WO | WO 99/53001 | 10/1999 |
| WO | WO 0224881 | 3/2002 |
| WO | WO 03070013 | 8/2003 |
| WO | WO 2004104193 | 12/2004 |
| WO | WO 2005063950 A1 * | 7/2005 |
| WO | WO 2005086900 | 9/2005 |

OTHER PUBLICATIONS

Xu, Lei and Diosady, Levente L. "Degumming", AOCS Press. 2004, Chapter 7, 31 pages.*

Dahlke, K. An enzymatic process for the physical refining of seed oils, Chemical Engineering Technology, 1998, 21 (3), pp. 278-281.*

Dahlke, Klaus, First Experiences with Enzymatic Oil Refining, INFORM, Dec. 1995, pp. 1284-1291, vol. 6, No. 12.

Ciofalo, Vince, Safety Evaluation of a Lipase Enzyme Preparation, Expressed in Pichia Pastoris, Intended for Use in the Degumming of Edible Vegetable Oil, www.sciencedirect.com, Nov. 5, 2005, Elsevier, World Wide Web, Regulatory Toxicology and Pharmacology. 2006, 45(1) , pp. 1-8.

Price, N.C. et al., *Fundamentals of Enzymology*, (3rd Edition 2003) Chapter 4, p. 118-153, Oxford University Press, Great Britain.

Ulbrich-Hofmann, R., *Enzymes in Lipid Modifications* (2000), pp. 218-262, Wiley-VCN GmbH & Co. KGaA, Weinheim.

E. H. Pryde, *Handbook of Soy Oil Processing*(1985), Chapter 2, pp. 13-31.

De Maria 1. et al., *Applied microbiology and biotechnology*, 2007, vol. 17, No. 2, pp. 290-300.

Clausen K., *European journal of lipid science and technology*, 2001, vol. 103, No. 6, pp. 333-340.

* cited by examiner

X = H, CHOLINE, ETHANOLAMINE, SERINE, INOSITOL, ETC.

ENZYMATIC DEGUMMING UTILIZING A MIXTURE OF PLA AND PLC PHOSPHOLIPASES WITH REDUCED REACTION TIME

FIELD OF THE INVENTION

This application relates to an enzymatic method for removing various phospholipids and lecithins (known collectively as "gums") from vegetable oils to produce a degummed oil or fat product that can be used for food production and/or non-food applications, preferably with an enzyme reaction period of less than about an hour. More particularly, this application relates to a method for the enzymatic treatment and removal of various phospholipids and lecithins in less than about an hour, which method can be practiced on either crude oils or water-degummed oils.

BACKGROUND OF THE INVENTION

Crude vegetable oils obtained from either pressing or solvent extraction methods are a complex mixture of triacylglycerols, phospholipids, sterols, tocopherols, free fatty acids, trace metals, and other minor compounds. It is desirable to remove the phospholipids, free fatty acids and trace metals in order to produce a quality salad oil with a bland taste, light color, and a long shelf life.

The removal of phospholipids generates almost all of the losses associated with the refining of vegetable oils. As illustrated in FIG. 1, phospholipids contain a phosphate group on one of the two ends of the glycerol backbone, whereas a triacylglycerol contains at least one fatty acid.

The phosphate group of the phospholipid is "hydrophilic" or "water-loving," meaning that the functional group X is attracted to water. The phospholipid's fatty acid chains R1 and R2 are "lipophilic" or "lipid-loving," meaning that they are attracted to lipids. Since the phospholipid molecule possesses both a hydrophilic functional group and lipophilic fatty acid chains, it is an excellent natural emulsifier.

The phospholipid's phosphate-containing functional group denoted in FIG. 1 as "X" determines the degree of its hydrophilic nature. The functional group X in FIG. 1 may be any of several of a variety of known types, a few of which are illustrated in FIG. 2.

Phospholipids containing the functional groups -choline and -ethanolamine have the greatest affinity for water, while the acids, acid salts (calcium, magnesium, and iron), and -inositol have much lower affinities for water. Phosphatidic acid and the salts of phosphatidic acid are commonly known as "Non Hydratable Phospholipids" or NHPs. Phospholipids are commonly measured in oil as "phosphorous content" in parts per million. Table 1 contains the typical amounts of phospholipids present in the major oilseed crops, and the distribution of the various functional groups as a percentage of the phospholipids present in the oil.

TABLE 1

Typical levels and phospholipid distributions for common oilseeds.
PHOSPHOLIPID COMPOSITION

|  | Soy Oil | Canola Oil | Sunflower Oil |
| --- | --- | --- | --- |
| P (ppm) | 400-1200 | 200-900 | 300-700 |
| PC (-choline) | 12%-46% | 25%-40% | 29%-52% |
| PE (-ethanolamine) | 8%-34% | 15%-25% | 17%-26% |
| PA (-acid) | 2%-21% | 10%-20% | 15%-30% |
| PI (-inositol) | 2%-15% | 2%-25% | 11%-22% |

Phospholipids can be partially or totally removed from vegetable oils through several different known means. The most commonly used processes in the industry are water degumming, acid degumming, caustic refining and enzymatic degumming.

Water Degumming

This technique is usually applied to crude oils containing a high amount of hydratable phospholipids. Due to its mild characteristics, the phospholipids obtained can be used as lecithin (a natural emulsifier). The oil obtained from this technique is generally referred to in the industry as being "degummed," despite being only partially degummed. Since water degummed oil still contains high amounts of phospholipids, especially non-hydratable phospholipids, the use of other process techniques, such as caustic refining or PLA1 enzyme degumming, can be required to produce a finished, high quality oil having high stability and low color.

In the water degumming process, water (1 to 5% w/w) is added to crude oil at 60-75° C. with vigorous mixing. The oil is then gently mixed from 15 to 60 minutes to aid the hydration of the phospholipids present in the oil, The hydration of the phospholipids or "gums" causes the gums to swell and agglomerate as a flocculent. The flocculent is an emulsion or mixture of hydrated gums and oil. The emulsion has a specific gravity higher than that of the oil and may be separated by settling, filtration, or the industrial practice of centrifugation. The centrifuge yields two streams, water degummed oil and wet gums. The water degumming process removes predominately only the hydratable phospholipids. The remaining phospholipids (50 to 250 ppm), measured as the salts of phosphatidic acid and/or PI, can be removed in subsequent processing operations.

The separated wet gums are an emulsified oil mixture containing at least one molecule of triacylglycerol (or oil) for every two molecules of phospholipid (or gum). This emulsified oil cannot be physically separated or recovered from the emulsion and is considered a process loss. The gums may be dried and sold as a food grade lecithin, but they are usually used as a by product in other applications such as animal feed or in an industrial process, with reduced economic value.

The oil loss through emulsification is significant, with a negative impact in the overall economic balance on the refined oil process cost.

Acid Degumming

This technique is usually applied to crude oils when the goal is the total removal of phospholipids. The oil obtained is usually called "super-degummed" or "totally degummed" in the industry.

Crude oil is treated with 250 to 2000 ppm of phosphoric acid or citric acid at 60-90° C. with vigorous mixing. The acid is allowed to react with the salts of the NHPs for a period of 10 to 90 minutes. The acid improves the hydrophilic nature of the NHPs, thus aiding in their removal. Water (1 to 5% w/w) is then added to the acid-treated crude oil at 60-75° C. with vigorous mixing. The oil is then gently mixed from 15 to 60 minutes to aid the hydration of the phospholipids. The hydration of the phospholipids or "gums" causes the gums to swell and agglomerate as a flocculent. The flocculent is an emulsion or mixture of hydrated gums and oil. The emulsion has a specific gravity higher than that of the oil and may be separated by settling, filtration, or the industrial practice of centrifugation. The centrifuge yields acid degummed oil and a wet gum. The acid degumming process removes most of the phospholipids, but enough still remain (25-100 ppm) in the degummed oil to require additional processing. For food applications, the acid degummed oil is usually submitted to bleaching and deodorization, a process known in the industry as "physical refining". The gums treated with acid are no longer usable for a food grade lecithin.

As in the water degumming process, the separated and dry gums in the acid degumming process contain at least one molecule of triacylglycerol (or oil) for every two molecules of phospholipid (or gum). This emulsified oil cannot be physically separated or recovered and is considered a process loss, with negative economic impact on the overall economic balance of the refined oil process cost.

Caustic Refining

This technique is usually applied to crude or water degummed oils when the goal is to remove all of the phospholipids and free fatty acids.

Crude or water degummed oil is treated with 200 to 1000 ppm of phosphoric acid or citric acid at 60-90° with vigorous mixing. The acid is allowed to react with the salts of the NHPs from 10 to 90 minutes. The acid improves the hydrophilic nature of the NHPs, thus aiding in their removal. A diluted sodium hydroxide solution (10-18% w/w) is added to the acid-treated oil at 65-75° C. The amount of sodium hydroxide (caustic) is based on the amount of free fatty acids present in the oil as well as an excess of between 0.05 to 0.20% on a dry basis. The caustic solution neutralizes the free fatty acids (producing sodium soaps), neutralizes the excess acid, and with the sodium soaps created, assists in hydrating and emulsifying all the remaining phospholipids.

The sodium hydroxide solution/oil is mixed for approximately 10 minutes then separated by settling, filtration, or industrially by centrifugation. The centrifuge yields a caustic treated oil and soapstock. The caustic treated oil is then "washed" with 10 to 20% softened water at 90-95° C. and centrifuged again. The oil from the centrifuge is known as "Once Refined" and the water is commonly known as "Wash Water". For food applications, the "once refined" oil is usually submitted for bleaching and deodorization to produce salad oil. An alternative to water washing is to treat the caustic treated oil with an absorbent silica gel, and filter out the residual soaps and phospholipids not removed in the initial centrifugation.

As with the water and acid degumming processes, the separated and dry gums in the caustic refining process contain one molecule of triacylglycerol (or oil) for every two molecules of phospholipid (or gum). This emulsified oil cannot be physically separated or recovered and is considered a process loss. Additionally, the sodium hydroxide will react with the neutral oil to form soaps, thereby further reducing the overall oil yield with negative economic impact in the overall economic balance on the refined oil process cost.

Enzymatic Treatment

Yet another refining technique used in the vegetable oil industry is "enzymatic refining" or "enzymatic degumming". Enzymatic degumming is used when the goal is the total removal of phospholipids. Generally, enzymatic degumming treatments of the prior art have been practiced on oils that have been degummed previously by one of the other methods, typically water degumming. For food applications, the enzyme degummed oil is sequentially submitted to bleaching and deodorization, a process known in the industry as "physical refining." Enzymatic degumming provides a better oil yield than water, acid, or caustic degumming, with improved economic results.

The enzymatic reaction changes the nature of the phospholipid, cleaving some of the phospholipid parts. This reduces the phospholipids' emulsification properties, so that less oil is lost when the gums are separated from the oil, thus saving oil. Enzymes exhibiting activity with phospholipids are commonly called "phospholipases". The types of phospholipase are based on the position on the phospholipid molecule at which the enzyme reacts, and are known as PLA1, PLA2, PLC, and PLD. The positions on the phospholipid molecule at which the different types of phospholipases react are illustrated in FIG. 3.

It may be seen in FIG. 3 that different types of phospholipases will yield different compounds upon reacting with the phospholipids. Further, each type of phospholipase has its own rate of reaction and its own optimal reaction conditions in terms of pH, water % and temperature. PLA when used alone generally requires a reaction time of at least about 4 hours, while PLC when used alone generally requires a reaction time of about one hour. It is known that enzymatic treatment should occur at a pH less than or equal to 8, in order to minimize undesirable oil saponification, but PLA has an optimum reaction pH of 4.5, while PLC has an optimum reaction pH of 7.0. Each enzyme also has different thermal tolerances. PLA enzymes will denature at about 50° C. while PLC enzymes will denature at about 65° C.

Sequences of amino acids with phospholipase activity are extensively reported in the literature and disclosed in patents, and some of those are reported to have activity on phospholipids present in vegetable oils. All this is known in the art.

One commercial PLA1 enzyme product with phospholipase activity is Novozymes' phospholipase A1 Lecitase® Ultra. This product is known to yield polar lyso-phospholipids and polar fatty acids when mixed with degummed oil with a 1-1.5% water citric acid-NaOH buffer at $4.5<pH<7.0$ and $40°\,C.<T<55°\,C.$, as described on Novozymes' Application Sheet Oils & Fats#2002-185255-01 and 2002-05894-03. The PLA1 selectively hydrolyzes the fatty acid opposite the phosphate functional group on the glycerol backbone, as illustrated in FIG. 4.

The resulting reaction yields a lyso-phospholipid and a fatty acid. The lyso-phospholipid molecule has lost one hydrophilic functional group, and the remaining alcohol group at the reaction site is hydrophilic. Now with two hydrophilic sites, the lyso-phospholipid molecule is water soluble, and has lost its emulsification properties. The PLA1 degumming process thus reduces refining losses by no longer removing any neutral oil with the gums, and the only loss is the original phospholipid molecule.

While enzymatic degumming offers significant advantages to oil processors, it also poses certain disadvantages. One disadvantage is that the reaction of the enzyme with the phospholipids can be slow and time consuming. In particular, the reaction of phospholipase A enzymes with phospholipids can take many hours, depending on reaction variables such as pH, temperature, relative concentrations, and mixing conditions. Such prolonged reaction times can have a significant negative impact on the overall economic value of enzymatic degumming processes. Because of the slowness of the PLA reaction, enzymatic degumming is typically carried out on oil compositions that have been first been subjected to water degumming. Thus, the oil must be degummed twice to obtain a product that has a phosphorous level low enough for its intended purposes.

It is known in the art that PLC enzymes react with a phospholipid by selectively hydrolyzing the phosphate functional group, as shown in FIG. 5. The resulting reaction yields a diacylglycerol ("DAG") and a phosphatidic group. The diacylglycerol molecule no longer has the phosphate functional group and does not need to be removed. The PLC degumming process reduces the refining loss by retaining the original phospholipid molecule, while removing only the phosphate functional group. However, PLC does not react with all of the phospholipids present in the oil. Generally, PLC does not react with either phosphatidic acid (PA) or phosphatidic inositol (PI), illustrated in FIG. 2. Yet both PA and PI are non-hydratable phosphatides that remain in oil after water degumming. Thus the PLC-treated oil must be further treated with caustic to remove the residual gums.

It is known that certain PLCs will react with only certain phosphatidic groups. For example, a PI-specific PLC, identified as PI-PLC, is known.

It is thus one aspect of the invention to provide a method for enzymatic degumming of oils wherein the enzymatic reaction rate is faster than in prior art enzymatic degumming processes, such that the enzymatic reaction has a duration of less than about one hour.

It is another aspect of the invention to provide a method for enhancing the reaction rate of a phospholipase A enzyme used in an enzymatic degumming process, such that the enzyme reaction has a duration of less than about one hour.

It is yet another aspect of the present invention to provide a method for degumming an oil composition in which both hydratable and non-hydratable phospholipids can be treated in a single process, the method including an enzyme reaction having a duration of less than about one hour.

The following references relate to the art of enzymatic degumming of oils.

U.S. Pat. No. 5,264,367 to Aalrust et al. describes the use of phospholipases A1, A2, or B to treat oil that has first been refined to 50 to 250 ppm phosphorous. The technology described in this patent is known commercially as Enzymax®. Aalrust states that since these enzymes attack lecithin, "it would make no sense to use the method of the invention on oils having a high content of lecithin, such as raw soybean oil." The reaction is carried out at a temperature of 20-80° C., with citric acid or a salt thereof at a pH range of 3-7. It is stated that the enzyme should be thoroughly distributed in the oil, with the enzyme-water solution present as droplets smaller than 10 μm in diameter. The form of measurement and calculations of the weight average were not disclosed. An emulsifier is used to dissolve the phospholipases obtained from pancreatin or pancreas products, which contain fat. Aalrust states that because the oil which is recovered contains less than 5 ppm of phosphorous, it is adaptable to be physically refined to edible oil. Later, details of the technology described by Aalrust were disclosed in several publications (Dahlke, K. and Eichelsbacher, M., Enzymax® and Alcon®—Lurgi's route to Physical Refining in Proceeding of the World Conference on Oilseed and Edible Oils Processing, Istanbul, Turkey, 1996, ed. Kaseoglu, Rhee and Wilson; Dalke, K. et al., First Experiences with Enzymatic Oil Refining, Inform, vol. 6, No. 12, December 1995). The data disclosed in these publications for industrial trials reinforce the use of the referred technology on oils with P content ranging from 40 to 180 ppm, and not higher. It is also disclosed that "The process does not require any special equipment. All pumps, agitators, mixers, and heat exchangers, as well as the centrifuge, are of standard design and can be procured from various suppliers." Dahlke, K. and Eichelsbacher, M., Enzymax® and Alcon®—Lurgi's route to Physical Refining in Proceeding of the World Conference on Oilseed and Edible Oils Processing, Istanbul, Turkey, 1996, ed. Kaseoglu, Ree and Wilson, page 56.

U.S. Pat. No. 5,532,163 to Yagi et al. discloses an enzymatic method using at least 30 weight parts water, and preferably 50-200 weight parts water, per 100 weight parts oil or fat, for the reaction of phospholipases A1, A2 or B with oil containing 100 to 10,000 ppm phosphorous. The oil is then washed with a 30% to 200% weight parts water or acidic aqueous solution per 100 weight parts oil or fat. The total water load required to utilize the process ranges from 60% to 400% w/w of oil processed. The production of such a large effluent in an industrial plant renders this method uneconomical.

U.S. Pat. No. 6,001,640 to Loeffler et al. discloses a process wherein one or more vegetable oils containing phosphorous-containing components are subjected to a mixture of phospholipases obtained from Aspergillus, the mixture comprising an enzyme having A1 activity, A2 activity, or both, and an enzyme having lysophospholipase activity. The patent states that since phospholipase would attack lecithin, it is not practical to use that method with oils with a high lecithin content, such as crude soybean oil.

Loeffler et al. disclose that the enzymatic reaction should be run at a pH of less than 4, and with the emulsion drop size being below 20 μm. The form of measurement and calculations of the emulsion drop size weight average were not disclosed. The patent states that the resulting product will have residual P of 15 ppm or less. It is known in the art that submitting the oil to pH as low as 4, or lower, will cause gums present in the oil to become hydrated and to separate from the reaction medium. The hydrated gums will act as emulsifiers, such that when they are separated they will carry oil with them, thus causing oil loss. No data on oil loss in the gums is presented.

U.S. Pat. No. 6,103,505 to Clausen et al. discloses the discovery and activity of certain phospholipases (A1, A2, or B) for use in the enzymatic removal of phospholipids, and a method for producing the enzymes. The enzymatic degumming process utilizes the method described in U.S. Pat. No. 5,264,367 without any additional process steps.

U.S. Pat. No. 6,127,137 to Hasida et al. discloses the discovery and activity of certain phospholipases capable of removing both of the fatty acyl groups present on a phospholipid molecule when mixed with degummed oil (50 to 250 ppm phosphorous) with a 0.5-5% water, pH from 1.5-3, temperature from 30-45° C., and a time of 1 to 12 hours.

U.S. Pat. No. 6,143,545 to Clausen et al. discloses the discovery and activity of certain phospholipases (A1, A2, or B) for use in the enzymatic removal of phospholipids, and a method for producing the enzymes. The enzymatic degumming process utilizes the method described in U.S. Pat. No. 5,264,367 without any additional process steps.

U.S. Pat. No. 6,548,633 to Edwards et al. discloses sequences of cDNA's encoding secreted proteins. At column 44, the patent states that the protein of that invention can be used in the enzyme degumming of vegetable oils as disclosed in U.S. Pat. No. 6,001,640, cited above. The patent further states in the same paragraph that the protein of that invention can be combined in a "cocktail" with other enzymes to improve feed utilization in animals.

U.S. patent application Ser. No. 10/556,816 of Dayton et al. discloses an improved enzymatic degumming process wherein the pH of the buffered enzymatic reaction is lowered to below 4.5 after the enzymatic reaction is completed, thereby eliminating the fouling of the equipment, particularly the heat exchangers and the separating centrifuge, that would result from precipitation of calcium and magnesium salts at the optimum pH required for the enzyme activity.

U.S. 2004/0005399 A1 of Chakrabarti et al. discloses an enzymatic method utilizing a single addition of enzyme and buffering system and a short retention/reaction time, followed by bleaching with 2-4% bleaching earth and 0-1% activated carbon, and then dewaxing to achieve an oil with a phosphorus content of 5 ppm. Both the bleaching process and dewaxing process will remove residual phosphorus from the oil. Additionally, Chakrabarti et al. states that the oil lost to the gums is in the range of 30-40% of the gums separated, suggesting that the enzymatic reaction did not go to completion, resulting in high oil losses due to emulsification of oil in the removed phospholipids.

U.S. 2005/0059130 A1 of Bojsen at al. discloses the discovery and activity of certain phospholipases for use in the enzymatic removal of phospholipids, and a method for producing the enzymes. The publication refers to the treatment of vegetable oil to reduce the content of phospholipids as disclosed in U.S. Pat. No. 5,264,367.

U.S. 2005/0108789A1 of Gramatikova et al., now U.S. Pat. No. 7,226,771 purports to disclose phospholipases (e.g., phospholipase A, B, C, D patatin enzymes) that efficiently cleave glycerolphosphate ester linkages in oils, such as vegetable oils, to generate a water extractable phosphorylated base and a diglyceride. At paragraph 108, the application further states that such phospholipases can be used for enzymatic degumming of vegetable oils, and that the PLC's of the invention can be used in addition to or in place of PLA1s and PLA2s in commercial oil degumming, such as in the ENZY-MAX® process, where phospholipids are hydrolyzed by PLA1 and PLA2. At paragraph 474, the application states that PLC may be used alone or with PLA to remove non-hydratable phospholipids from oil that previously has been water degummed, but does not provide reaction conditions for use of the two enzymes together. As the optimum reaction conditions of PLA enzyme and PLC enzyme are different, this statement in the application with no working examples does not teach one skilled in the art how to use PLA and PLC enzymes simultaneously. The application further states that phospholipases C, D1 and D2 may be employed in the enzymatic degumming of previously degummed and non-degummed (crude) oils and as an aid to caustic refining.

U.S. patent application Ser. No. 11/668,921, filed Jan. 30, 2007, in the name of Dayton et al., assigned to the common assigned herein and incorporated herein by reference in its entirety, discloses enzymatic degumming of oils using a mixture of PLA and PLC enzymes.

SUMMARY OF THE INVENTION

The invention relates to a method for degumming an oil composition, the method comprising
(a) providing an oil composition containing a quantity of phospholipids,
(b) contacting said oil composition simultaneously with one or more phospholipase A enzymes and one or more phospholipase C enzymes, under conditions sufficient for the enzymes to react with the phospholipids to create phospholipid reaction products, and
(c) separating the phospholipids reaction products from the oil composition, the remaining oil composition after the separation being a degummed oil composition,
whereby during step (b) the reaction of said one or more phospholipase A enzymes proceeds at a faster rate than it would in the absence of said one or more phospholipase C enzymes, and wherein the reaction of step (b) continues for a duration of less than about one hour.

The amount of water necessary for the process of the present invention advantageously has been reduced to less than about 3%, and preferably about 1.5-2.0%.

The pH of the system can be adjusted either before or after the addition of one or all of the enzymes to the oil composition. The yield of oil is maximized based on the phospholipid composition contained in the crude.

Specifically, this invention relates to ain improvement in the method disclosed in the above-referenced U.S. patent application Ser. No. 11/668,921, filed Jan. 30, 2007, in the name of Dayton et al., in which method both a Phospholipase C (PLC) enzyme and a Phospholipase A (PLA) enzyme are used together in an enzyme reaction to remove phospholipids present in oil. That invention related to adding in combination a Phospholipase C (PLC) and/or Phosphatidyl-Inositol specific Phospholipase C (PI-PLC) with Phospholipase A1 (PLA1) and/or Phospholipase A2 (PLA2) to maximize oil yield and reduce the amount of waste products produced. As disclosed therein, it was found that the kinetics of the enzyme reactions proceed much more rapidly than expected when the two enzymes are used together than when either one is used separately. Further, it has been found that the reactions proceed more rapidly than expected even if the reaction conditions are not optimized for at least one of the enzymes. Now, in accordance with the present invention, it has been found that the reaction can proceed in less than about one hour, and can proceed as quickly as about thirty minutes.

Advantageously, the oil treated can be either a crude oil or a water-degummed oil. The enzymes can be added to the oil either separately or together, but for the present invention the two enzymes will be in simultaneous contact with the oil. In accordance with the invention, enzymatic reaction parameters such as water concentration, temperature, pH, agitation time, and enzyme concentration can be controlled to optimize the reaction for a particular enzyme combination in a particular oil system.

DETAILED DESCRIPTION OF THE INVENTION

Figure 1:
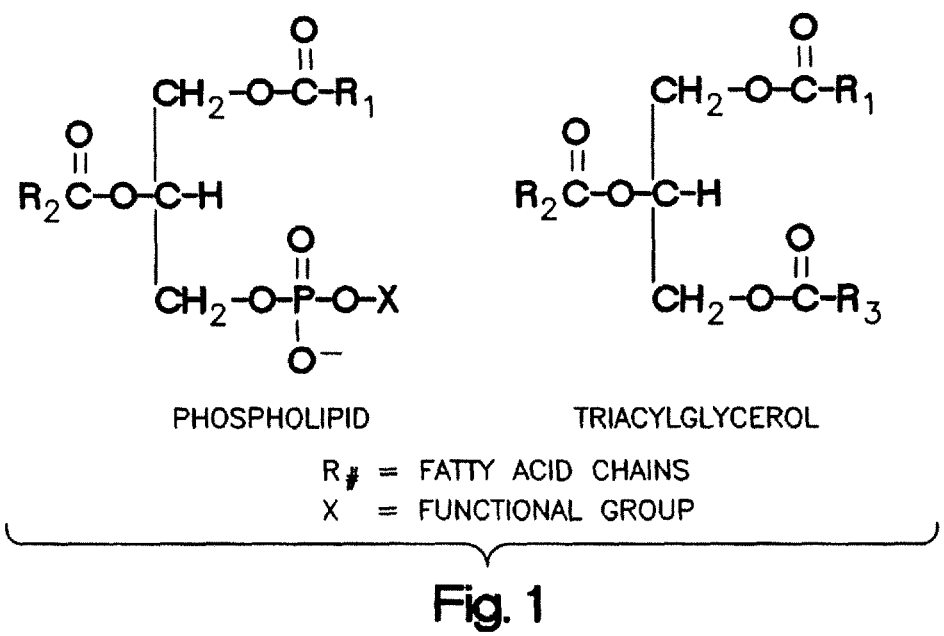
FIG. 1 is illustrates the chemical structures of generic phospholipids and generic triacylglycerols.
Figure 2:
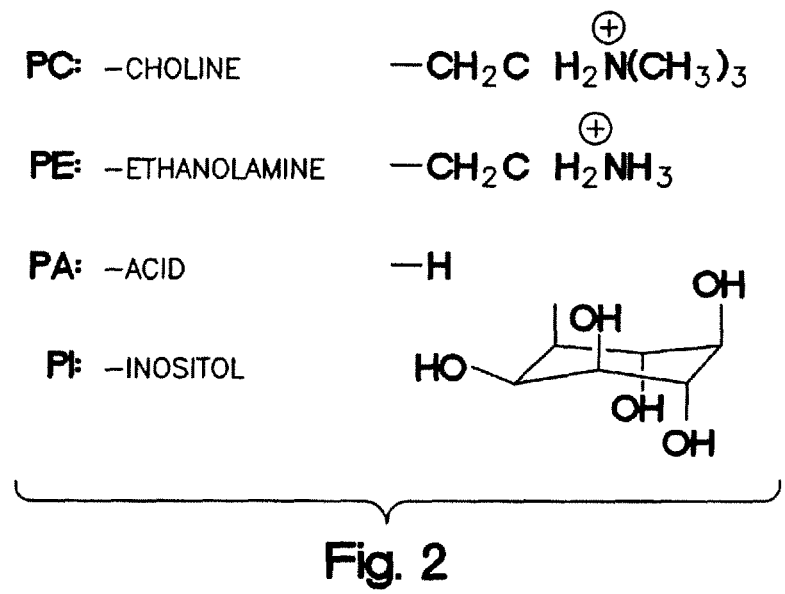
FIG. 2 illustrates functional groups and structures for common phospholipids.
Figure 3:
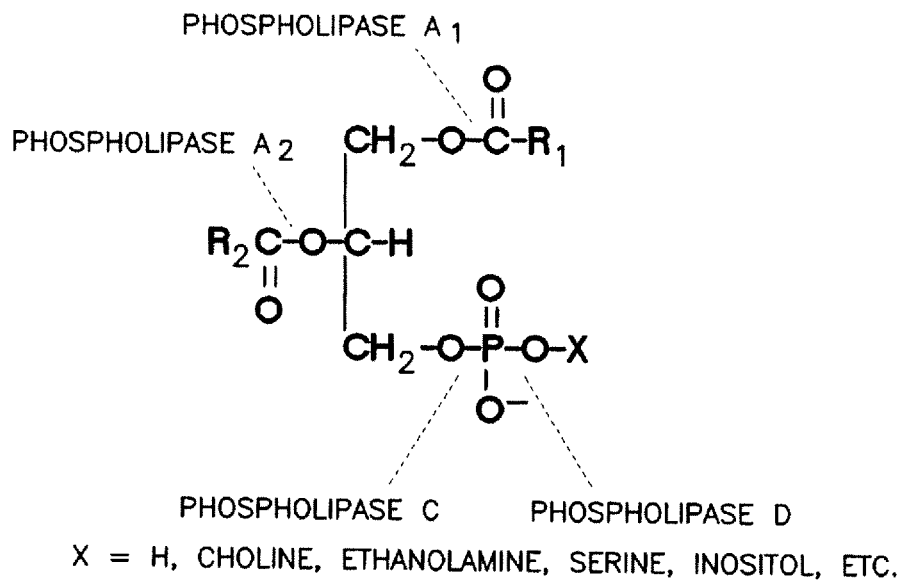
FIG. 3 illustrates the positions on the phospholipid molecule at which the different types of phospholipases react.
Figure 4:
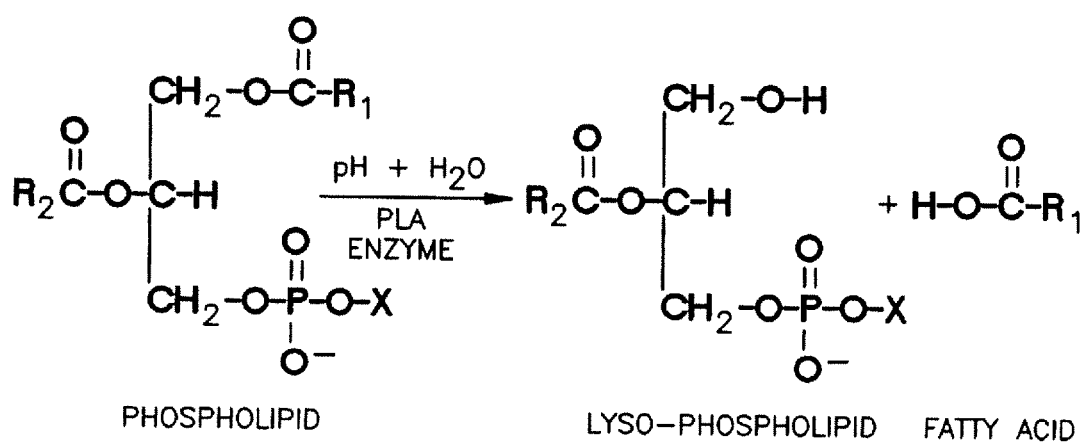
FIG. 4 illustrates the reaction of a phospholipid with a PLA 1 enzyme and the resulting products.
Figure 5:
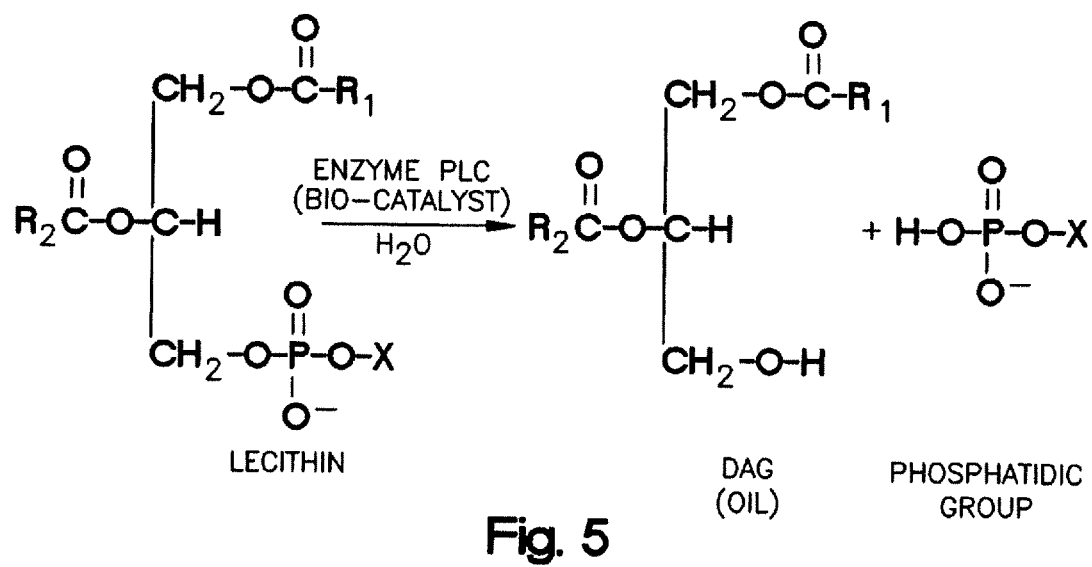
FIG. 5 illustrates the reaction of a phospholipid with a PLC enzyme and the resulting products

The present invention relates to an improvement in a process for enzymatically degumming an oil composition. Specifically, in an enzymatic degumming process such as that disclosed in the aforementioned U.S. patent application Ser. No. 11/668,921, conducted with a combination of a phospholipase C enzyme with a phospholipase A enzyme to provide a degummed oil product with a lower phosphorus content in a shorter reaction time than would be achieved with phospholipase A alone, it has been found that surprisingly the reaction can proceed in less than about one hour, and can proceed as quickly as about thirty minutes. This is particularly unexpected because PLA when used alone generally requires a reaction time of at least about 4 hours, while PLC when used alone generally requires a reaction time of about one hour. Moreover PLA has an optimum reaction pH of 4.5, while PLC has an optimum reaction pH of 7.0. Each enzyme also has different thermal tolerances. The PLA enzyme will denature at about 50° C. while the PLC enzyme will denature at about 65° C. In addition, it is known in the art that the thermal stability of enzymes can be improved via site specific mutations. Such cloned enzymes can be thermally stable at temperatures as high as 80° C., and the use of such cloned enzymes is contemplated in the present invention.

The reduction of the reaction time is evidenced by the PLA. When used in combination with PLC, the reaction time is dramatically reduced to less than about 1 hour, even under acidic reaction conditions which are not optimum for PLC. The inventors of the present application further have found that under proper conditions it is possible to reduce the reaction time to as low as about 30 minutes.

While in the aforementioned U.S. patent application Ser. No. 11/668,921, filed Jan. 30, 2007, in the name of Dayton et al the water concentration was about 3%, it has been found that the water concentration can be adjusted to meet the needs of a particular processing environment. Thus, the water concentration can be decreased to about 1-2%, and particularly to about 1.5%, where it is desired to reduce the amount of wastewater produced by the process. Alternatively, the water concentration can be increased to about 4-5%, and particularly to about 4.5%, where it is desired to increase the efficiency of the degumming process.

It is an advantage of the present invention that the oil to be degummed can be either crude oil, or previously degummed by one of the prior art methods. It is a distinct advantage to the oil processor to be able to accomplish the oil degumming in a single step. Oils that can be treated in accordance with the present invention may include but are not limited to the following; canola oil, castor oil, coconut oil, coriander oil, corn oil, cottonseed oil, hazelnut oil, hempseed oil, linseed oil, mango kernel oil, meadowfoam oil, neat's foot oil, olive oil, palm oil, palm kernel oil, palm olein, peanut oil, rapeseed oil, rice bran oil, safflower oil, sasanqua oil, soybean oil, sunflower seed oil, tall oil, tsubaki oil, and vegetable oil.

The phospholipase A enzyme used in the method of the present invention can be either a phospholipase A1 enzyme or a phospholipase A2 enzyme. The phospholipase C enzyme used in the present invention can be either a phospholipase C or an inositol specific phospholipase C. Many varieties of enzymes in the phospholipase A and phospholipase C families are available commercially; and it is contemplated that such enzymes and their equivalents will be suitable for use in the present invention.

In the method of the invention, the different phospholipases used together in an enzymatic degumming process of the present invention can be mixed together before being added to the oil to be treated. Alternatively, they can be added to the oil separately, either sequentially or simultaneously. Whether added sequentially or simultaneously, the enzymatic reaction will proceed at some point with both enzymes present in the reaction mixture.

The degumming process of the present invention is carried out at a pH below about 8, preferable between about 3-7, and most preferably between about 4-5. The pH of the enzyme degumming process can be achieved by the addition of known buffers. Citric acid and sodium hydroxide are well known to be suited to this purpose. Other buffering agents can be used as needed to adjust the pH under specific reaction conditions.

The temperature of the enzymatic degumming process of the present invention can be in the range of about 40-80° C., preferably in the range of about 40-60° C., and more preferably in the range of about 45-55° C. It has been found that, surprisingly, under the methods of the present invention PLA degumming can proceed at a temperature above its own optimum of 45° C., and closer to the optimum operating temperature of PLC, without excessive denaturing.

The method of the present invention provides a single step degumming process in which the phospholipids content of an oil, even a crude oil, can be reduced to less than 50 ppm P, preferably less than 20 ppm P, more preferably less than 10 ppm P, and most preferably less than 5 ppm P.

After the enzymatic degumming has been completed and the degummed oil has been separated from the gums, the degummed oil can be subjected to further processing steps known in the art such as bleaching or deodorizing, as may be necessary or desirable depending on the end use for which the degummed oil product is intended.

Various preferred embodiments of the invention are set forth in the examples below, along with control examples using conditions of the prior art. In each of the examples below, the overhead mixer was a Heidolph mixer model Elector KG with a flat blade paddle; operated at 90 rpm for normal agitation and 350 rpm for vigorous agitation. The centrifuge was a De Laval Gyro—Tester installed with "The Bowl Unit" for continuous separation. The centrifuge bowl was closed with the plug screws installed. Shear mixing was accomplished with an Ultra-Turrax homogenizer SD-45 with a G450 rotor stator at 10,000 rpm. The PLA1 enzyme was Lecitase® Ultra (lot number LYN050070) sold by Novozymes A/S of Denmark, and having a concentration of 11.2 Units/mg. The PLA2 enzyme was Rohalase® MPL (Lot number Ch: 4738) sold by AB Enzymes located in Germany, and having a concentration of 2000 Units/mg. The PLC enzyme was Purifine™ sold by Diversa Corporation of San Diego, Calif. For examples 1-12, the PLC was Lot BD16449, having a concentration of 205 Units/mg. For Examples 13-38, the PLC was Lot 90BU002A1, having a concentration of 27.5 Units/mg. The amount of phospholipids remaining in the treated oil was measured as ppm P in accordance with the method of American Oil Chemists' Society Official Method Ca 20-99, "Analysis of Phosphorus in Oil by Inductively Coupled Plasma Optical Emission Spectroscopy."

Example 1

Control: Water Degumming 1965.4 grams of crude soybean oil containing 746 ppm phosphorous was heated to 70-75° C. under normal agitation utilizing an overhead mixer. To the warm oil, 39.4 grams of de-ionized water was added with vigorous agitation for 1 minute. The mixer was slowed to normal speed (90 rpm) to allow the gums to flocculate for 30 minutes. The oil was then centrifuged, and the separated oil and wet gums were collected. The residual phosphorous in the water-degummed oil was 80.7 ppm.

Example 2

Control: Single Enzyme Degumming with Phospholipase A1 (PLA1)

1997.9 g of crude soybean oil containing 746 ppm phosphorous was heated to 75-80° C. under agitation utilizing an overhead mixer. 2.0 grams of 50% w/w solution of citric acid was added and the mixture was sheared for 1 minute. The oil underwent normal agitation for one hour with an overhead mixer. The oil was allowed to cool with agitation at normal speed until the oil temperature was at 40-45° C., then 1.8 milliliters of 4 molar sodium hydroxide solution was added, and the mixture was shear mixed for 10 seconds. The citric acid and caustic formed a weak buffer with a pH of 4.5. With the temperature maintained at 40-45° C., first 60.0 grams of de-ionized water was added and the mixture was shear mixed 1 minute, then 0.1044 grams of Novozymes' Lecitase® Ultra PLA1 was added and the entire mixture was sheared for 1 minute. The oil mixture was agitated at normal speed with an overhead mixer for 4 hours at a temperature range of 41-48° C. The enzyme treated oil was then centrifuged; and the separated oil and wet gums were collected. The residual phosphorous in the PLA1-degummed oil was 31.7 ppm.

Example 3

Control: Single Enzyme Degumming with Phospholipase C (PLC)

2011.1 grams of crude soybean oil containing 746 ppm phosphorous was heated to 55-60° C. under normal agitation utilizing an overhead mixer. 60.3 grams of de-ionized water was added and the mixture was shear mixed for 1 minute. 0.1051 grams of Diversa's Purfine™ (PLC lipase BD16449 containing 205 U/mg) was added and the mixture was sheared for 1 minute. The oil mixture underwent normal agitation for 1 hour at 50-63° C. The enzyme treated oil was then centrifuged, and the separated oil and wet gums were collected. The residual phosphorous in the PLC degummed oil was 70.9 ppm.

Example 4

Control: PLC Followed by PLA Degumming

In this control example, the oil sample is reacted with each enzyme separately under the reaction conditions optimum for that enzyme, in accordance with the prior art. 2110.5 grams of crude soybean oil containing 560.1 ppm phosphorous was heated to 60° C. under normal agitation. 63 grams of de-ionized water and 0.1123 grams of Diversa's Purfine™ (PLC lipase BD16449 containing 205 U/mg) were added and the mixture sheared for 1 minute. The oil mixture was agitated at normal speed for 1 hour at 55-56° C. The oil was then centrifuged, and the oil and wet gums were collected. To create a buffer of pH 4.5, first 2.0 grams of 50% w/w solution of citric acid was added to the PLC-degummed oil, the mixture was sheared for 1 minute, and then agitated for one hour at normal speed with an overhead mixer; then 1.8 milliliters of 4 molar sodium hydroxide solution was added, and the oil mixture was shear mixed for 10 seconds. 59 grams of de-ionized water was added and the mixture was shear mixed 1 minute. With the buffer established, 0.1061 grams of Novozymes' Lecitase® Ultra PLA1 was added and the entire mixture was sheared for 1 minute. The oil was agitated at normal speed for 4 hours at a temperature range of approximately 45° C. The oil was then centrifuged; the separated oil and wet gums were collected. The residual phosphorous in the PLC then PLA1 sequentially degummed oil was 3.2 ppm.

Example 5

PLC and PLA1 Together, Neutral pH with a 1 Hour Reaction Time at 45° C.

2004.9 grams of crude soybean oil containing 560.1 ppm phosphorus was heated to 45° C. under normal agitation. With the oil at a neutral pH, 60 grams of de-ionized water, 0.1037 grams of Diversa's Purfine™ (PLC enzyme) and 0.1076 grams of Novozymes' Lecitase® Ultra (PLA1 enzyme) were added to the oil and the entire mixture was sheared for 1 minute. The oil and enzyme mixture was agitated at normal speed for 1 hour at a temperature of approximately 45° C. The oil was then centrifuged, and the separated oil and wet gums were collected. The oil treated with the PLC and PLA1 combined enzyme mixture at a neutral pH and 45° C. with one hour of reaction time produced a degummed oil with a residual phosphorous of 13.2 ppm.

This residual phosphorous value is significantly lower than that achieved with either PLA alone under its optimum conditions (Example 2), or PLC alone under its optimum conditions (Example 3).

Example 6

PLC and PLA1 Together, Neutral pH with a 4 Hour Reaction Time at 45° C.

2003.7 grams of crude soybean oil containing 560.1 ppm phosphorus was heated to 45° C. under normal agitation. 60 grams of de-ionized water, 0.1040 grams of Diversa's Purfine™ (PLC enzyme) and 0.1085 grams of Novozymes' Lecitase® Ultra (PLA1 enzyme) were added and the entire mixture was sheared for 1 minute. The oil mixture was agitated at normal speed for 4 hours at a temperature of approximately 45° C. The oil was then centrifuged, and the separated oil and wet gums were collected. The process using the PLC and PLA1 combined enzyme mixture with four hours of reaction time at a neutral pH produced a degummed oil with a residual phosphorous of 10.5 ppm.

This residual phosphorous value is only a slight improvement over that achieved in Example 5, indicating that an increase of the reaction time from one hour to four hours did not make a significant difference in the efficacy of the degumming process.

Example 7

PLC and PLA1 Together, 4.5 pH with a 1 Hour Reaction Time at 45° C.

2021.4 g of crude soybean oil containing 547.9 ppm phosphorous was heated to 75-80° C. under normal agitation utilizing an overhead mixer. 2.0 grams of 50% w/w solution of citric acid was added and sheared for 1 minute. The oil mixture was agitated at normal speed for one hour. The oil was allowed to cool until the temperature reached 40-45° C., then 1.8 milliliters of 4 molar sodium hydroxide solution was added, and the mixture was shear mixed for 10 seconds. 61.0 grams of de-ionized water, 0.1184 grams of Diversa's Purfine™ (PLC enzyme) and 0.1038 grams of Novozymes' Lecitase® Ultra (PLA1 enzyme) were added and the entire mixture was sheared for 1 minute. The oil mixture was agitated at normal speed for 1 hour at a temperature of approximately 45° C. The oil was then centrifuged, and the separated oil and wet gums were collected. The process using the PLC and PLA1 combined enzyme mixture with one hour of reaction time at a pH of 4.5 and a temperature of 45° C. produced a degummed oil with a residual phosphorous of 2.4 ppm.

This residual phosphorous value is about the same, and even slightly better, than that achieved in Example 4 wherein each enzyme was reacted separately and at its own optimum conditions. Surprisingly, degumming efficacy is just as good when the two enzymes are run together at a reaction time not optimum for PLA, and at a pH and temperature not optimum for PLC, as for the two enzymes run separately, each at its own optimum conditions.

Example 8

PLC and PLA1 Together, 4.5 pH with a 4 Hour Reaction Time at 45° C.

2069.3 g of crude soybean oil containing 547.9 ppm phosphorous was heated to 75-80° C. under normal agitation. 2.0 grams of 50% w/w solution of citric acid was added, and the mixture was sheared for 1 minute, and then agitated at normal speed for one hour. The mixture was allowed to cool to 40-45° C., then 1.8 milliliters of 4 molar sodium hydroxide solution was added, and the mixture was shear mixed for 10 seconds. 63 grams of de-ionized water, 0.1112 grams of Diversa's Purfine™ (PLC enzyme) and 0.1258 grams of Novozymes' Lecitase® Ultra (PLA1 enzyme) were added and the entire mixture was sheared for 1 minute. The oil mixture was agitated at normal speed for 4 hours at a temperature of approximately 45° C. The oil mixture was then centrifuged, and the separated oil and wet gums were collected. The process using the PLC and PLA1 combined enzyme mixture with four hours of reaction time at a pH of 4.5 produced a degummed oil with a residual phosphorous of 2.5 ppm.

This residual phosphorous value is about the same as that achieved in Example 7 indicating that an increase of the reaction time from one hour to four hours did not make a significant difference in the efficacy of the degumming process.

Example 9

PLC and PLA1 Together, 4.5 pH with a 1 Hour Reaction Time at 55° C.

1985.2 g of crude soybean oil containing 547.9 ppm phosphorous was heated to 75-80° C. under normal agitation. 2.0 grams of 50% w/w solution of citric acid was added and the mixture was sheared for 1 minute, then agitated a normal speed for one hour. The mixture was allowed to cool to 40-45° C., then 1.8 milliliters of 4 molar sodium hydroxide solution was added, and the mixture was shear mixed for 10 seconds. 63.0 grams of de-ionized water, 0.1085 grams of Diversa's Purfine™ (PLC enzyme) and 0.1045 grams of Novozymes' Lecitase® Ultra (PLA1 enzyme) were added and the entire mixture was sheared for 1 minute. The oil mixture was agitated at normal speed for 1 hour at a temperature of 55° C. The oil was then centrifuged; the separated oil and wet gums were collected. The process using the PLC and PLA1 combined enzyme mixture with one hour of reaction time at a pH of 4.5 and a reaction temperature of 55° C. produced a degummed oil with a residual phosphorous of 2.3 ppm.

This residual phosphorous value is about the same as that achieved in Examples 7 and 8, indicating that an increase of the reaction temperature from about 45° C. to about 55° C. did not make a significant difference in the efficacy of the degumming process, even though PLA1 would normally be expected to denature at a temperature above 50° C.

Example 10

PLC and 2 Times PLA1 Concentration Together, 4.5 pH with a 1 Hour Reaction Time at 45° C.

1992.2 g of crude soybean oil containing 547.9 ppm phosphorous was heated to 75-80° C. under agitation at normal speed. 2.0 grams of 50% w/w solution of citric acid was added and the mixture was sheared for 1 minute, then agitated for one hour. The mixture was allowed to cool to 40-45° C., then 1.8 milliliters of 4 molar sodium hydroxide solution was added, and the mixture was shear mixed for 10 seconds. To the mixture were added 60 grams of de-ionized water, 0.1319 grams of Diversa's Purfine™ (PLC enzyme) and 0.2139 grams of Novozymes' Lecitase® Ultra (PLA1 enzyme), and the entire mixture was sheared for 1 minute. The oil mixture was agitated at normal speed for 1 hour at a temperature range of 45° C. The oil mixture was then centrifuged; the separated oil and wet gums were collected. The process using the PLC and twice the concentration of PLA1 combined enzyme mixture with one hour of reaction time at a pH of 4.5 produced a degummed oil with a residual phosphorous of 7.0 ppm.

This residual phosphorous value is acceptable for certain applications but not quite as good as that achieved in Examples 7-9, indicating that, surprisingly, increasing the dosage of PLA1 does not result in improved efficacy of the degumming process, even under reaction conditions optimum for PLA1.

Example 11

PLC and PLA2 Together, 4.5 pH with 1 Hour Retention Lime it 45° C.

1998.4 grams of crude soybean oil containing 341.2 ppm phosphorous was heated to 75-80° C. under normal agitation utilizing an overhead mixer. 2.0 grams of 50% w/w solution of citric acid was added and sheared for 1 minute. The oil underwent normal agitation for 1 hour with an overhead mixer. The oil was allowed to cool with agitation at normal speed until the oil temperature was 40° C., then 1.8 milliliters of 4 molar sodium hydroxide solution was added, and the mixture was shear mixed for 10 seconds. The citric acid and caustic formed a weak buffer with a pH of 4.5. With the temperature maintained at 40-45° C., 0.1112 grams of Diversa's Purfine™ ((PLC lipase BD16449 containing 205 U/mg) and 0.2094 grams Rohalase® MPL (Lot number Ch: 4738) sold by AB Enzymes were added followed by 60 grams of de-ionized water and the entire mixture was shear mixed for 60 seconds. The oil mixture was agitated at normal speed for 60 minutes at a temperature of 40-45° C. The enzyme treated oil was then centrifuged; and the separated oil and wet gums were collected. The residual phosphorous in the PLC and PLA2 combined enzyme mixture at neutral pH produced a degummed oil with a residual phosphorous of 3.3 ppm.

This example is similar to Example 7 above, but for the substitution of PLA2 for PLA1. The low residual phosphorous level in the finished product demonstrates that PLA2 can function about equally well as PLA1 in the method of the present invention.

Example 12

PLC and PLA2 Together, 4.5 pH with 4 Hour Retention Time at 45° C.

1998.4 grams of crude soybean oil containing 341.2 ppm phosphorous was heated to 75-80° C. under normal agitation utilizing an overhead mixer. 2.0 grams of 50% w/w solution of citric acid was added and sheared for 1 minute. The oil underwent normal agitation for 1 hour with an overhead mixer. The oil was allowed to cool with agitation at normal speed until the oil temperature was 40° C., then 1.8 milliliters of 4 molar sodium hydroxide solution was added, and the mixture was shear mixed for 10 seconds. The citric acid and caustic formed a weak buffer with a pH of 4.5. With the temperature maintained at 40-45° C., 0.1038 grams of Diversa's Purifine™ ((PLC lipase BD16449 containing 205 U/mg) and 0.2047 grams Rohalase® MPL (Lot number Ch: 4738) sold by AB Enzymes were added followed by 60 grams of de-ionized water and the entire mixture was shear mixed for 60 seconds. The oil mixture was agitated at normal speed for 4 hours at a temperature of 40-45° C. The enzyme treated oil was then centrifuged; and the separated oil and wet gums were collected. The residual phosphorous in the PLC and PLA2 combined enzyme mixture at neutral pH produced a degummed oil with a residual phosphorous of 5.8 ppm.

This example illustrates that increasing the reaction time from one to four hours did not result in better degumming, and in fact resulted in a higher level of residual phosphorous.

The results of the foregoing Examples 1-12 are summarized in Table 2 below.

TABLE 3

| Variable | Levels Enzyme Addition | |
|---|---|---|
| | Sequential | Simultaneous |
| PLC Amount (ppm active) | 10 | 20 | 30 |
| PLA Amount (ppm active) | 0.5 | 1.0 | 2.0 |
| Agitation time (sec) | 45 | 60 | 120 |
| pH | 4.5 | 5.0 | 7.0 |
| Water (%) | 1.5 | 3.0 | 4.5 |
| Temperature (° C.) | 40 | 50 | 60 |
| Reaction Time (min) | 30 | 60 | 120 |

Sequential—each enzyme was added separately although both enzymes were in contact with the oil mixture during at least part of the reaction time Simultaneous—both enzymes were added at the same time pH—The pH at which the enzymes are exposed to the oil Temperature—Temperature at which the enzymes are exposed to the oil Agitation time—The time that the mixture is agitated at high speed after addition of each enzyme Reaction Time—Total time that at least one enzyme is in contact with oil

TABLE 2

| Example | Enzyme Addition | PLC (ppm Active Enzyme) | PLA1 (ppm Active Enzyme) | PLA2 (ppm Active Enzyme) | Reaction Time (min.) | Temp. (C.) | pH | Water (%) | Phos. (ppm) |
|---|---|---|---|---|---|---|---|---|---|
| 1 | none | | | | 30 | 70-75 | 7 | 2.0 | 80.7 |
| 2 | Single | | 0.6 | | 240 | 41-48 | 4.5 | 3.0 | 31.7 |
| 3 | Single | 10.8 | | | 60 | 50-63 | 7 | 3.0 | 70.9 |
| 4 | Sequential | 11.5 | 0.6 | | 60, 240 | 55, 45 | 4.5 | 3.1 | 3.2 |
| 5 | Simultaneous | 10.6 | 0.6 | | 60 | 45 | 7 | 3.0 | 13.2 |
| 6 | Simultaneous | 10.7 | 0.6 | | 240 | 45 | 7 | 3.0 | 10.5 |
| 7 | Simultaneous | 12.1 | 0.6 | | 60 | 45 | 4.5 | 3.0 | 2.4 |
| 8 | Simultaneous | 11.4 | 0.7 | | 240 | 45 | 4.5 | 3.1 | 2.5 |
| 9 | Simultaneous | 11.1 | 0.6 | | 60 | 55 | 4.5 | 3.1 | 2.3 |
| 10 | Simultaneous | 13.5 | 1.2 | | 60 | 45 | 4.5 | 3.0 | 7.0 |
| 11 | Simultaneous | 11.4 | | 209 | 60 | 45 | 4.5 | 3.0 | 3.3 |
| 12 | Simultaneous | 10.6 | | 205 | 240 | 45 | 4.5 | 3.0 | 5.8 |

EXAMPLES 13-30

A Design of Experiments (DOE) was set up to determine the effects of certain process control variables for the enzymatic degumming process, as set forth in Table 3 below.

These operational variables were evaluated in eighteen separate trials presented herein as Examples 13-30. The values of each variable tested in each example 13-30 are set forth in Table 4 below.

TABLE 4

| Ex. | Enzyme Addition | PLC (ppm Active Enzyme) | PLA1 (ppm Active Enzyme) | Reaction Time (minutes) | Temp. (C.) | pH | Water (%) | Agitation Time (seconds) |
|---|---|---|---|---|---|---|---|---|
| 13 | Sequential | 20 | 1 | 120 | 40 | 5 | 1.5 | 120 |
| 14 | Simultaneous | 20 | 1 | 60 | 60 | 7 | 1.5 | 45 |
| 15 | Sequential | 10 | 1 | 30 | 40 | 7 | 4.5 | 60 |
| 16 | Sequential | 10 | 2 | 60 | 50 | 4.5 | 1.5 | 120 |
| 17 | Sequential | 20 | 2 | 30 | 50 | 7 | 3.0 | 45 |
| 18 | Sequential | 10 | 0.5 | 120 | 60 | 5 | 3.0 | 45 |
| 19 | Simultaneous | 30 | 2 | 30 | 60 | 5 | 1.5 | 60 |
| 20 | Simultaneous | 10 | 2 | 120 | 60 | 7 | 4.5 | 120 |
| 21 | Simultaneous | 20 | 2 | 120 | 40 | 4.5 | 3.0 | 60 |
| 22 | Sequential | 30 | 2 | 60 | 40 | 5 | 4.5 | 45 |
| 23 | Sequential | 30 | 1 | 30 | 60 | 4.5 | 3.0 | 120 |
| 24 | Simultaneous | 30 | 1 | 120 | 50 | 4.5 | 4.5 | 45 |

TABLE 4-continued

| Ex. | Enzyme Addition | PLC (ppm Active Enzyme) | PLA1 (ppm Active Enzyme) | Reaction Time (minutes) | Temp. (C.) | pH | Water (%) | Agitation Time (seconds) |
|---|---|---|---|---|---|---|---|---|
| 25 | Simultaneous | 10 | 1 | 60 | 50 | 5 | 3.0 | 60 |
| 26 | Sequential | 20 | 0.5 | 60 | 60 | 4.5 | 4.5 | 60 |
| 27 | Sequential | 30 | 0.5 | 120 | 50 | 7 | 1.5 | 60 |
| 28 | Simultaneous | 30 | 0.5 | 60 | 40 | 7 | 3.0 | 120 |
| 29 | Simultaneous | 20 | 0.5 | 30 | 50 | 5 | 4.5 | 120 |
| 30 | Simultaneous | 10 | 0.5 | 30 | 40 | 4.5 | 1.5 | 45 |

Example 13

1999.1 grams of crude soybean oil containing 769.5 ppm of phosphorous was heated to 75-80° C. under normal agitation utilizing an overhead mixer. 2.0 grams of 50% w/w solution of citric acid was added and sheared for 1 minute. The oil underwent normal agitation for 1 hour with an overhead mixer. The oil was allowed to cool with agitation at normal speed until the oil temperature was 40° C., then 2.4 milliliters of 4 molar sodium hydroxide solution was added, and the mixture was shear mixed for 10 seconds. The citric acid and caustic formed a weak buffer with a pH of 5.0. With the temperature maintained at 40° C., 1.5008 grams of Diversa's Purifine™ (PLC lipase lot number 90BU002A1) was added followed by 30 grams of de-ionized water and the entire mixture was shear mixed for 120 seconds. The oil mixture was agitated at normal speed for 60 minutes. With the temperature maintained at 40° C., 0.2132 grams of Novozymes' Lecitase® Ultra (PLA1 lipase lot number LYN05007) was added and the entire mixture was shear mixed for 120 seconds. The oil mixture was agitated at normal speed for 60 minutes at a temperature of 40° C. The enzyme treated oil was then centrifuged; and the separated oil and wet gums were collected. The residual phosphorous in the PLC then PLA1 sequential degummed oil was 6.5 ppm.

Example 14

2010.5 grams of crude soybean oil containing 785.1 ppm of phosphorous was cooled to 60° C. under normal agitation utilizing and overhead mixer. With the temperature maintained at 60° C., 1.5316 grams of Diversa's Purifine™ (PLC lipase lot number 90BU002A1) and 0.2073 grams Novozymes' Lecitase® Ultra (PLA1 lipase lot number LYN05007) were added followed by 30 grams of de-ionized water and the entire mixture was shear mixed for 45 seconds. The oil mixture was agitated at normal speed for 60 minutes at a temperature of 60° C. The enzyme treated oil was then centrifuged; and the separated oil and wet gums were collected. The residual phosphorous in the PLC and PLA1 combined enzyme mixture at neutral pH produced a degummed oil with a residual phosphorous of 109.6 ppm.

Example 15

1994.5 grams of crude soybean oil containing 785.1 ppm of phosphorous was cooled to 40° C. under normal agitation utilizing and overhead mixer. With the temperature maintained at 40° C., 0.754 grams of Diversa's Purifine™ (PLC lipase lot number 90BU002A1) was added followed by 90 grams of de-ionized water and the entire mixture was shear mixed for 60 seconds. The oil mixture was agitated at normal speed for 15 minutes. With the temperature maintained at 40° C., 0.2242 grams of Novozymes' lecitasen Ultra (PLA1 lipase lot number LYN05007) was added and the entire mixture was shear mixed for 60 seconds. The oil mixture was agitated at normal speed for 15 minutes at a temperature of 40° C. The enzyme treated oil was then centrifuged; and the separated oil and wet gums were collected. The residual phosphorous in the PLC then PLA1 sequential degummed oil was 27.4 ppm.

Example 16

2002.0 grams of crude soybean oil containing 785.1 ppm of phosphorous was heated to 75-80° C. under normal agitation utilizing an overhead mixer. 2.0 grams of 50% w/w solution of citric acid was added and sheared for 1 minute. The oil underwent normal agitation for 1 hour with an overhead mixer. The oil was allowed to cool with agitation at normal speed until the oil temperature was 50° C., then 1.8 milliliters of 4 molar sodium hydroxide solution was added, and the mixture was shear mixed for 10 seconds. The citric acid and caustic formed a weak buffer with a pH of 4.5. With the temperature maintained at 50° C., 0.7498 grams of Diversa's Purifine™ (PLC lipase lot number 90BU002A1) was added followed by 30 grams of de-ionized water and the entire mixture was shear mixed for 120 seconds. The oil mixture was agitated at normal speed for 30 minutes. With the temperature maintained at 50° C., 0.4064 grams of Novozymes' Lecitase® Ultra (PLA1 lipase lot number LYN05007) was added and the entire mixture was shear mixed for 120 seconds. The oil mixture was agitated at normal speed for 30 minutes at a temperature of 50° C. The enzyme treated oil was then centrifuged; and the separated oil and wet gums were collected. The residual phosphorous in the PLC then PLA1 sequential degummed oil was 7.6 ppm.

Example 17

2010.7 grams of crude soybean oil containing 785.1 ppm of phosphorous was heated to 50° C. under normal agitation utilizing and overhead mixer. With the temperature maintained at 50° C., 1.4981 grams of Diversa's Purifine™ (PLC lipase lot number 90BU002A1) was added followed by 60 grams of de-ionized water and the entire mixture was shear mixed for 45 seconds. The oil mixture was agitated at normal speed for 15 minutes. With the temperature maintained at 50° C., 0.4143 grams of Novozymes' Lecitase® Ultra (PLA1 lipase lot number LYN05007) was added and the entire mixture was shear mixed for 45 seconds. The oil mixture was agitated at normal speed for 15 minutes at a temperature of 50° C. The enzyme treated oil was then centrifuged; and the separated oil and wet gums were collected. The residual phosphorous in the PLC then PLA1 sequential degummed oil was 79.3 ppm.

Example 18

2005.3 grams of crude soybean oil containing 742.9 ppm of phosphorous was heated to 75-80° C. under normal agitation utilizing an overhead mixer. 2.0 grams of 50% w/w solution of citric acid was added and sheared for 1 minute. The oil underwent normal agitation for 1 hour with an overhead mixer. The oil was allowed to cool with agitation at normal speed until the oil temperature was 60° C., then 2.4 milliliters of 4 molar sodium hydroxide solution was added, and the mixture was shear mixed for 10 seconds. The citric acid and caustic formed a weak buffer with a pH of 5.0. With the temperature maintained at 60° C., 0.7491 grams of Diversa's Purifine™ (PLC lipase lot number 90BU002A1) was added followed by 60 grams of de-ionized water and the entire mixture was shear mixed for 45 seconds. The oil mixture was agitated at normal speed for 60 minutes. With the temperature maintained at 60° C., 0.1220 grams of Novozymes' Lecitase® Ultra (PLA1 lipase lot number LYN05007) was added and the entire mixture was shear mixed for 45 seconds. The oil mixture was agitated at normal speed for 60 minutes at a temperature of 60° C. The enzyme treated oil was then centrifuged; and the separated oil and wet gums were collected. The residual phosphorous in the PLC then PLA1 sequential degummed oil was 2.2 ppm.

Example 19

2000.4 grams of crude soybean oil containing 742.9 ppm of phosphorous was heated to 75-80° C. under normal agitation utilizing an overhead mixer. 2.0 grams of 50% w/w solution of citric acid was added and sheared for 1 minute. The oil underwent normal agitation for 1 hour with an overhead mixer. The oil was allowed to cool with agitation at normal speed until the oil temperature was 60° C., then 2.4 milliliters of 4 molar sodium hydroxide solution was added, and the mixture was shear mixed for 10 seconds. The citric acid and caustic formed a weak buffer with a pH of 5.0. With the temperature maintained at 60° C., 2.2270 grams of Diversa's Purifine™ (PLC lipase lot number 90BU002A1) and 0.3937 grams Novozymes' Lecitase® Ultra (PLA1 lipase lot number LYN05007) were added followed by 30 grams of de-ionized water and the entire mixture was shear mixed for 60 seconds. The oil mixture was agitated at normal speed for 30 minutes at a temperature of 60° C. The enzyme treated oil was then centrifuged; and the separated oil and wet gums were collected. The residual phosphorous in the PLC and PLA1 combined enzyme mixture at pH 5.0 produced a degummed oil with a residual phosphorous of 7.8 ppm.

Example 20

2006.3 grams of crude soybean oil containing 719.3 ppm of phosphorous was heated to 60° C. under normal agitation utilizing and overhead mixer. With the temperature maintained at 60° C., 0.7561 grams of Diversa's Purifine™ (PLC lipase lot number 90BU002A1) and 0.4098 grams Novozymes' Lecitase® Ultra (PLA1 lipase lot number LYN05007) were added followed by 90 grams of de-ionized water and the entire mixture was shear mixed for 120 seconds. The oil mixture was agitated at normal speed for 120 minutes at a temperature of 60° C. The enzyme treated oil was then centrifuged; and the separated oil and wet gums were collected. The residual phosphorous in the PLC and PLA1 combined enzyme mixture at neutral pH produced a degummed oil with a residual phosphorous of 64.1 ppm.

Example 21

1998.5 grams of crude soybean oil containing 719.3 ppm of phosphorous was heated to 75-80° C. under normal agitation utilizing an overhead mixer. 2.0 grams of 50% w/w solution of citric acid was added and sheared for 1 minute. The oil underwent normal agitation for 1 hour with an overhead mixer. The oil was allowed to cool with agitation at normal speed until the oil temperature was 40° C., then 1.8 milliliters of 4 molar sodium hydroxide solution was added, and the mixture was shear mixed for 10 seconds. The citric acid and caustic formed a weak buffer with a pH of 4.5. With the temperature maintained at 40° C., 1.4798 grams of Diversa's Purifine™ (PLC lipase lot number 90BU002A1) was added and 0.4018 grams Novozymes' Lecitase® Ultra (PLA1 lipase lot number LYN05007) was added followed by 60 grams of de-ionized water and the entire mixture was shear mixed for 60 seconds. The oil mixture was agitated at normal speed for 120 minutes at a temperature of 40° C. The enzyme treated oil was then centrifuged; and the separated oil and wet gums were collected. The residual phosphorous in the PLC and PLA1 combined enzyme mixture at pH 4.5 produced a degummed oil with a residual phosphorous of 5.5 ppm.

Example 22

2001.3 grams of crude soybean oil containing 719.3 ppm of phosphorous was heated to 75-80° C. under normal agitation utilizing an overhead mixer. 2.0 grams of 50% w/w solution of citric acid was added and sheared for 1 minute. The oil underwent normal agitation for 1 hour with an overhead mixer. The oil was allowed to cool with agitation at normal speed until the oil temperature was 40° C., then 2.4 milliliters of 4 molar sodium hydroxide solution was added, and the mixture was shear mixed for 10 seconds. The citric acid and caustic formed a weak buffer with a pH of 5.0. With the temperature maintained at 40° C., 2.2580 grams of Diversa's Purifine™ (PLC lipase lot number 90BU002A1) was added followed by 90 grams of de-ionized water and the entire mixture was shear mixed for 45 seconds. The oil mixture was agitated at normal speed for 30 minutes. With the temperature maintained at 40° C., 0.4126 grams of Novozymes' Lecitase® Ultra (PLA1 lipase lot number LYN05007) was added and the entire mixture was shear mixed for 45 seconds. The oil mixture was agitated at normal speed for 30 minutes at a temperature of 40° C. The enzyme treated oil was then centrifuged; and the separated oil and wet gums were collected. The residual phosphorous in the PLC and PLA1 sequential treated degummed oil had a residual phosphorous of 2.1 ppm.

Example 23

2002.0 grams of crude soybean oil containing 747.3 ppm of phosphorous was heated to 75-80° C. under normal agitation utilizing an overhead mixer. 2.0 grams of 50% w/w solution of citric acid was added and sheared for 1 minute. The oil underwent normal agitation for 1 hour with an overhead mixer. The oil was allowed to cool with agitation at normal speed until the oil temperature was 60° C., then 1.8 milliliters of 4 molar sodium hydroxide solution was added, and the mixture was shear mixed for 10 seconds. The citric acid and caustic formed a weak buffer with a pH of 4.5. With the temperature maintained at 60° C., 2.2194 grams of Diversa's Purifine™ (PLC lipase lot number 90BU002A1) followed by 60 grams of de-ionized water were added and the entire mixture was shear mixed for 120 seconds. The oil mixture was agitated at normal speed for 15 minutes. With the temperature maintained at 60° C., 0.2198 grams of Novozymes' Lecitase® Ultra (PLA1 lipase lot number LYN05007) was added and the entire mixture was shear mixed for 120 seconds. The oil mixture was agitated at normal speed for 15 minutes at a temperature of 60° C. The enzyme treated oil was then centrifuged; and the separated oil and wet gums were collected. The residual phosphorous in the PLC and PLA1 sequential treated degummed oil had a residual phosphorous of 4.6 ppm.

Example 24

2000.8 grams of crude soybean oil containing 747.3 ppm of phosphorous was heated to 75-80° C. under normal agitation utilizing an overhead mixer. 2.0 grams of 50% w/w solution of citric acid was added and sheared for 1 minute. The oil underwent normal agitation for 1 hour with an overhead mixer. The oil was allowed to cool with agitation at normal speed until the oil temperature was 50° C., then 1.8 milliliters of 4 molar sodium hydroxide solution was added, and the mixture was shear mixed for 10 seconds. The citric acid and caustic formed a weak buffer with a pH of 4.5. With the temperature maintained at 50° C., 2.2500 grams of Diversa's Purifine™ (PLC lipase lot number 90BU002A1) was added and 0.2216 grams Novozymes' Lecitase® Ultra (PLA1 lipase lot number LYN05007) was added followed by 90 grams of de-ionized water and the entire mixture was shear mixed for 45 seconds. The oil mixture was agitated at normal speed for 120 minutes at a temperature of 50° C. The enzyme treated oil was then centrifuged; and the separated oil and wet gums were collected. The residual phosphorous in the PLC and PLA1 combined enzyme mixture produced a degummed oil with a residual phosphorous of 1.8 ppm.

Example 25

1998.9 grams of crude soybean oil containing 747.3 ppm of phosphorous was heated to 75-80° C. under normal agitation utilizing an overhead mixer. 2.0 grams of 50% w/w solution of citric acid was added and sheared for 1 minute. The oil underwent normal agitation for 1 hour with an overhead mixer. The oil was allowed to cool with agitation at normal speed until the oil temperature was 50° C., then 2.4 milliliters of 4 molar sodium hydroxide solution was added, and the mixture was shear mixed for 10 seconds. The citric acid and caustic formed a weak buffer with a pH of 5.0. With the temperature maintained at 50° C., 0.7445 grams of Diversa's Purifine™ (PLC lipase lot number 90BU002A1) was added and 0.2042 grams Novozymes' Lecitase® Ultra (PLA1 lipase lot number LYN05007) was added followed by 60 grams of de-ionized water was and the entire mixture was shear mixed for 60 seconds. The oil mixture was agitated at normal speed for 60 minutes at a temperature of 50° C. The enzyme treated oil was then centrifuged; and the separated oil and wet gums were collected. The residual phosphorous in the PLC and PLA1 combined enzyme mixture produced a degummed oil with a residual phosphorous of 7.2 ppm.

Example 26

1997.3 grams of crude soybean oil containing 810.8 ppm of phosphorous was heated to 75-80° C. under normal agitation utilizing an overhead mixer. 2.0 grams of 50% w/w solution of citric acid was added and sheared for 1 minute. The oil underwent normal agitation for 1 hour with an overhead mixer. The oil was allowed to cool with agitation at normal speed until the oil temperature was 60° C., then 1.8 milliliters of 4 molar sodium hydroxide solution was added, and the mixture was shear mixed for 10 seconds. The citric acid and caustic formed a weak buffer with a pH of 4.5. With the temperature maintained at 60° C., 1.5189 grams of Diversa's Purifine™ (PLC lipase lot number 90BU002A1) followed by 90 grams of de-ionized water was added and the entire mixture was shear mixed for 60 seconds. The oil mixture was agitated at normal speed for 30 minutes. With the temperature maintained at 60° C., 0.1119 grams of Novozymes' Lecitase® Ultra (PLA1 lipase lot number LYN05007) was added and the entire mixture was shear mixed for 60 seconds. The oil mixture was agitated at normal speed for 30 minutes at a temperature of 60° C. The enzyme treated oil was then centrifuged; and the separated oil and wet gums were collected. The residual phosphorous in the PLC and PLA1 sequential treated degummed oil had a residual phosphorous of 2.2 ppm.

Example 27

12010.0 grams of crude soybean oil containing 810.8 ppm of phosphorous was cooled to 50° C. under normal agitation utilizing and overhead mixer. With the temperature maintained at 50° C., 2.2608 grams of Diversa's Purifine™ (PLC lipase lot number 90BU002A1) followed by 30 grams of de-ionized water was added and the entire mixture was shear mixed for 60 seconds. The oil mixture was agitated at normal speed for 60 minutes. With the temperature maintained at 50° C., 0.1172 grams of Novozymes' Lecitase® Ultra (PLA1 lipase lot number LYN05007) was added and the entire mixture was shear mixed for 60 seconds. The oil mixture was agitated at normal speed for 60 minutes at a temperature of 50° C. The enzyme treated oil was then centrifuged; and the separated oil and wet gums were collected. The residual phosphorous in the PLC and PLA1 sequential treated degummed oil at a neutral pH had a residual phosphorous of 72.6 ppm.

Example 28

2005.1 grams of crude soybean oil containing 810.8 ppm of phosphorous was heated to 40° C. under normal agitation utilizing and overhead mixer. With the temperature maintained at 40° C., 2.2622 grams of Diversa's Purifine™ (PLC lipase lot number 90BU002A1) and 0.1031 grams Novozymes' Lecitase® Ultra (PLA1 lipase lot number LYN05007) was added followed by 60 grams of de-ionized water and the entire mixture was shear mixed for 120 seconds. The oil mixture was agitated at normal speed for 60 minutes at a temperature of 40° C. The enzyme treated oil was then centrifuged; and the separated oil and wet gums were collected. The residual phosphorous in the PLC and PLA1 combined enzyme mixture at a neutral pH produced a degummed oil with a residual phosphorous of 61.5 ppm.

Example 29

2006.3 grams of crude soybean oil containing 795.3 ppm of phosphorous was heated to 75-80° C. under normal agitation utilizing an overhead mixer. 2.0 grams of 50% w/w solution of citric acid was added and sheared for 1 minute. The oil underwent normal agitation for 1 hour with an overhead mixer. The oil was allowed to cool with agitation at normal speed until the oil temperature was 50° C., then 2.4 milliliters of 4 molar sodium hydroxide solution was added, and the mixture was shear mixed for 10 seconds. The citric acid and caustic formed a weak buffer with a pH of 5.0. With the temperature maintained at 50° C., 1.5373 grams of Diversa's Purifine™ (PLC lipase lot number 90BU002A1) and 0.1168 grams Novozymes' Lecitase® Ultra (PLA1 lipase lot number LY05007) was added followed by 90 grams of de-ionized water and the entire mixture was shear mixed for 120 seconds. The oil mixture was agitated at normal speed for 30 minutes at a temperature of 50° C. The enzyme treated oil was then centrifuged; and the separated oil and wet gums were collected. The residual phosphorous in the PLC and PLA1 combined enzyme mixture at a pH of 5.0 produced a degummed oil with a residual phosphorous of 1.9 ppm.

Example 30

2006.1 grams of crude soybean oil containing 795.3 ppm of phosphorous was heated to 75-80° C. under normal agitation utilizing an overhead mixer. 2.0 grams of 50% w/w solution of citric acid was added and sheared for 1 minute. The oil underwent normal agitation for 1 hour with an overhead mixer. The oil was allowed to cool with agitation at normal speed until the oil temperature was 40° C., then 1.8 milliliters of 4 molar sodium hydroxide solution was added, and the mixture was shear mixed for 10 seconds. The citric acid and caustic formed a weak buffer with a pH of 4.5. With the temperature maintained at 40° C., 0.7736 grams of Diversa's Purifine™ (PLC lipase lot number 90BU002A1) and 0.1072 grams Novozymes' Lecitase® Ultra (PLA1 lipase lot number LYN05007) was added followed by 30 grams of de-ionized water and the entire mixture was shear mixed for 45 seconds. The oil mixture was agitated at normal speed for 30 minutes at a temperature of 40° C. The enzyme treated oil was then centrifuged; and the separated oil and wet gums were collected. The residual phosphorous in the PLC and PLA1 combined enzyme mixture at a pH of 4.5 produced a degummed oil with a residual phosphorous of 13.7 ppm.

The results of Examples 13-30 in terms of phosphorous level achieved is set forth in Table 5 below.

TABLE 5

| Ex. | Enzyme Addition | PLC (ppm Active Enzyme) | PLA1 (ppm Active Enzyme) | Reaction Time (minutes) | Temp (C.) | pH | Water (%) | Agitation Time (seconds) | Phos (ppm) |
|---|---|---|---|---|---|---|---|---|---|
| 13 | Sequential | 20.6 | 1.2 | 120 | 40 | 5 | 1.5 | 120 | 6.5 |
| 14 | Simultaneous | 21.1 | 1.2 | 60 | 60 | 7 | 1.5 | 45 | 109.6 |
| 15 | Sequential | 10.4 | 1.3 | 30 | 40 | 7 | 4.5 | 60 | 27.4 |
| 16 | Sequential | 10.3 | 2.3 | 60 | 50 | 4.5 | 1.5 | 120 | 7.6 |
| 17 | Sequential | 20.6 | 2.3 | 30 | 50 | 7 | 3.0 | 45 | 79.3 |
| 18 | Sequential | 10.3 | 0.7 | 120 | 60 | 5 | 3.0 | 45 | 2.2 |
| 19 | Simultaneous | 30.6 | 2.2 | 30 | 60 | 5 | 1.5 | 60 | 7.8 |
| 20 | Simultaneous | 10.4 | 2.3 | 120 | 60 | 7 | 4.5 | 120 | 64.1 |
| 21 | Simultaneous | 20.3 | 2.3 | 120 | 40 | 4.5 | 3.0 | 60 | 5.5 |
| 22 | Sequential | 31.0 | 2.3 | 60 | 40 | 5 | 4.5 | 45 | 2.1 |
| 23 | Sequential | 30.5 | 1.2 | 30 | 60 | 4.5 | 3.0 | 120 | 4.6 |
| 24 | Simultaneous | 30.9 | 1.2 | 120 | 50 | 4.5 | 4.5 | 45 | 1.8 |
| 25 | Simultaneous | 10.2 | 1.4 | 60 | 50 | 5 | 3.0 | 60 | 7.2 |
| 26 | Sequential | 20.9 | 0.6 | 60 | 60 | 4.5 | 4.5 | 60 | 2.2 |
| 27 | Sequential | 31.1 | 0.7 | 120 | 50 | 7 | 1.5 | 60 | 72.6 |
| 28 | Simultaneous | 31.1 | 0.6 | 60 | 40 | 7 | 3.0 | 120 | 61.5 |
| 29 | Simultaneous | 21.1 | 0.7 | 30 | 50 | 5 | 4.5 | 120 | 1.9 |
| 30 | Simultaneous | 10.6 | 0.6 | 30 | 40 | 4.5 | 1.5 | 45 | 13.7 |

Figure 6:
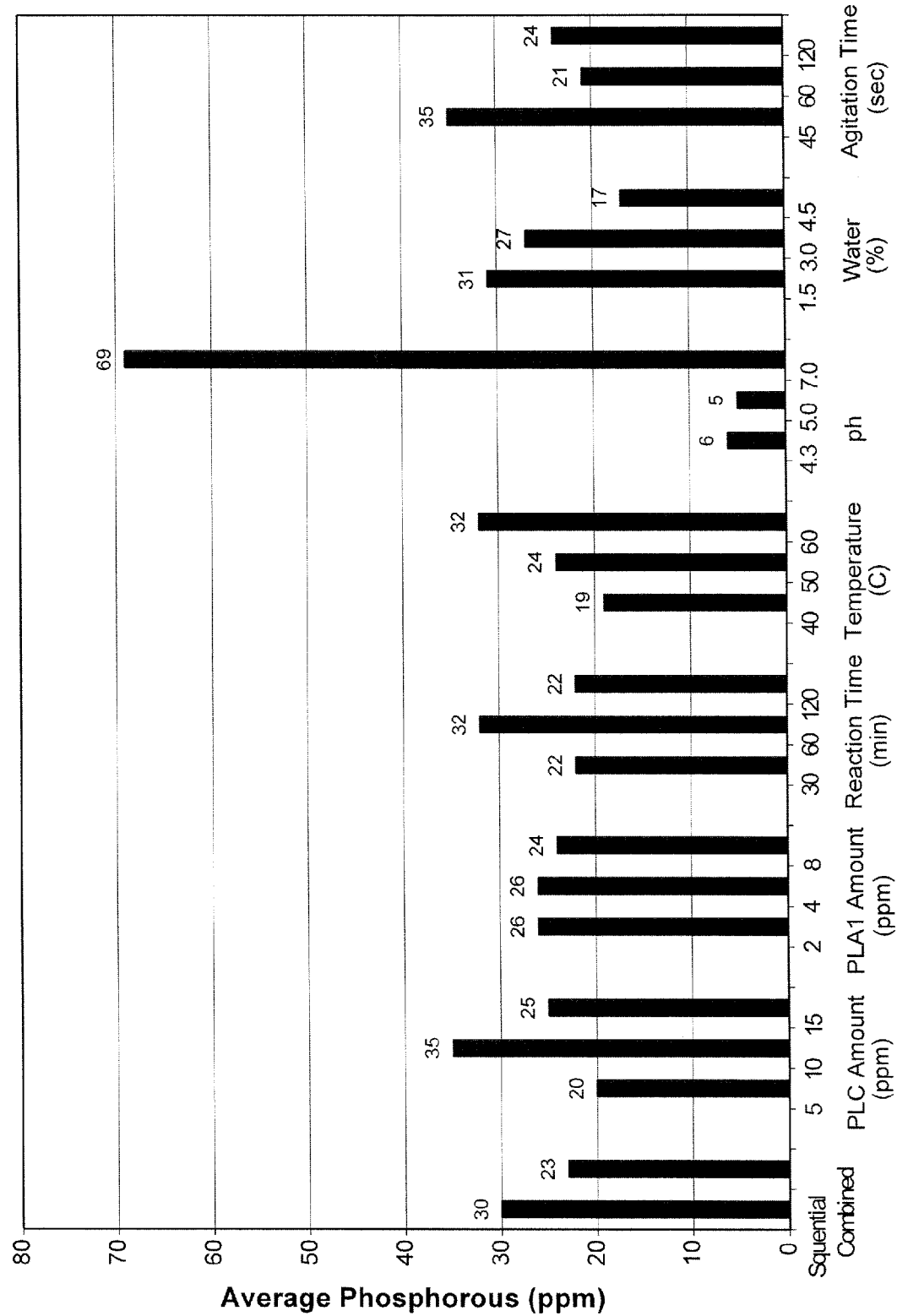
FIG. 6 is a graph summarizing the results of Examples 13-30, in which the average residual phosphorous in the degummed sample is plotted for each level of each experimental factor being evaluated.

A summary of the above experimental runs is illustrated in the graph shown in FIG. 6, which is a plot of the average final phosphorous amount at each level of each factor.

At a neutral pH, optimum for the PLC enzyme, the combination of the two enzymes failed to produce an oil with acceptable phosphorous values allowing for the oil to be physically refined. However, at an acidic pH, optimum for the PLA enzyme, the combination of enzymes added sequentially or together produced acceptable residual phosphorous levels in oils that would allow them to be physically refined. When an acidic pH is employed, only one of the experimental runs failed to produce an oil with a residual phosphorous of less than 10 ppm. Example 30 had a residual phosphorous level greater than 10 (13.7 ppm), and was produced with the lowest levels of both enzymes, the lowest temperature, the lowest percentage of water, the shortest mixing and agitation times, and the most acidic pH.

A synergetic effect was discovered between the enzyme combination allowing the reaction to go to completion in less than 30 minutes, compared with 1 hour for the PLC enzymes or 4 hours for the PLA enzymes. Additional testing was completed to verify the effect of very short reaction time; the results are set forth in Table 6 below. In these additional tests, the pH was maintained at 4.5, in view of the finding above that a lower pH produced significantly more favorable results than a neutral pH. The amount of PLA1 also was held constant at 0.5 ppm, as it was determined above that increasing the amount of PLA1 above this level did not result in more effective degumming. Further, in each of these examples the enzymes were added simultaneously rather than sequentially, in view of the determination above that simultaneous addition of enzymes produced better degumming results than sequential addition. Further, in an industrial process it is advantageous to limit the total process time, total equipment, and dedicated assets.

TABLE 6

| Example | Enzyme Addition | PLC (ppm Active Enzyme) | PLA1 (ppm Active Enzyme) | Reaction Time (minutes) | Temp (C.) | pH | Water (%) | Agitation Time (seconds) |
|---|---|---|---|---|---|---|---|---|
| 31 | Simultaneous | 20 | 0.5 | 120 | 40 | 4.5 | 2.0 | 120 |
| 32 | Simultaneous | 10 | 0.5 | 120 | 60 | 4.5 | 4.5 | 45 |
| 33 | Simultaneous | 10 | 0.5 | 30 | 40 | 4.5 | 4.5 | 120 |
| 34 | Simultaneous | 20 | 0.5 | 30 | 60 | 4.5 | 2.0 | 45 |
| 35 | Simultaneous | 20 | 0.5 | 120 | 40 | 4.5 | 4.5 | 45 |
| 36 | Simultaneous | 20 | 0.5 | 30 | 60 | 4.5 | 4.5 | 120 |
| 37 | Simultaneous | 10 | 0.5 | 30 | 40 | 4.5 | 2.0 | 45 |
| 38 | Simultaneous | 10 | 0.5 | 120 | 60 | 4.5 | 2.0 | 120 |

Example 31

2003.6 grams of crude soybean oil containing 784.8 ppm of phosphorous was heated to 75-80° C. under normal agitation utilizing an overhead mixer. 2.0 grams of 50% w/w solution of citric acid was added and sheared for 1 minute. The oil underwent normal agitation for 1 hour with an overhead mixer. The oil was allowed to cool with agitation at normal speed until the oil temperature was 40° C., then 1.8 milliliters of 4 molar sodium hydroxide solution was added, and the mixture was shear mixed for 10 seconds. The citric acid and caustic formed a weak buffer with a pH of 4.5. With the temperature maintained at 40° C., 1.4603 grams of Diversa's Purifine™ (PLC lipase lot number 90BU002A1) and 0.1021 grams Novozymes' Lecitase® Ultra (PLA1 lipase lot number LYN05007) was added followed by 40 grams of de-ionized water and the entire mixture was shear mixed for 120 seconds. The oil mixture was agitated at normal speed for 120 minutes at a temperature of 40° C. The enzyme treated oil was then centrifuged; and the separated oil and wet gums were collected. The residual phosphorous in the PLC and PLA1 combined enzyme mixture at a pH of 4.5 produced a degummed oil with a residual phosphorous of 10.7 ppm.

Example 32

2004.8 grams of crude soybean oil containing 784.8 ppm of phosphorous was heated to 75-80° C. under normal agitation utilizing an overhead mixer. 2.0 grams of 50% w/w solution of citric acid was added and sheared for 1 minute. The oil underwent normal agitation for 1 hour with an overhead mixer. The oil was allowed to cool with agitation at normal speed until the oil temperature was 60° C., then 1.8 milliliters of 4 molar sodium hydroxide solution was added, and the mixture was shear mixed for 10 seconds. The citric acid and caustic formed a weak buffer with a pH of 4.5. With the temperature maintained at 60° C., 0.7509 grams of Diversa's Purifine™ (PLC lipase lot number 90B3U002A1) and 0.1105 grams Novozymes' Lecitase® Ultra (PLA1 lipase lot number LYN05007) was added followed by 90 grams of de-ionized water and the entire mixture was shear mixed for 45 seconds. The oil mixture was agitated at normal speed for 120 minutes at a temperature of 60° C. The enzyme treated oil was then centrifuged; and the separated oil and wet gums were collected. The residual phosphorous in the PLC and PLA1 combined enzyme mixture at a pH of 4.5 produced a degummed oil with a residual phosphorous of 6.7 ppm.

Example 33

2000.4 grams of crude soybean oil containing 697.7 ppm of phosphorous was heated to 75-80° C. under normal agitation utilizing an overhead mixer. 2.0 grams of 50% w/w solution of citric acid was added and sheared for 1 minute. The oil underwent normal agitation for 1 hour with an overhead mixer. The oil was allowed to cool with agitation at normal speed until the oil temperature was 40° C., then 1.8 milliliters of 4 molar sodium hydroxide solution was added, and the mixture was shear mixed for 10 seconds. The citric acid and caustic formed a weak buffer with a pH of 4.5. With the temperature maintained at 40° C., 0.7530 grams of Diversa's Purifine™ (PLC lipase lot number 90BU002A1) and 0.1022 grams Novozymes' Lecitase® Ultra (PLA1 lipase lot number LYN05007) was added followed by 90 grams of de-ionized water and the entire mixture was shear mixed for 120 seconds. The oil mixture was agitated at normal speed for 30 minutes at a temperature of 40° C. The enzyme treated oil was then centrifuged; and the separated oil and wet gums were collected. The residual phosphorous in the PLC and PLA1 combined enzyme mixture at a pH of 4.5 produced a degummed oil with a residual phosphorous of 2.2 ppm.

Example 34

1999.4 grams of crude soybean oil containing 714.2 ppm of phosphorous was heated to 75-80° C. under normal agitation utilizing an overhead mixer. 2.0 grams of 50% w/w solution of citric acid was added and sheared for 1 minute. The oil underwent normal agitation for 1 hour with an overhead mixer. The oil was allowed to cool with agitation at normal speed until the oil temperature was 60° C., then 1.8 milliliters of 4 molar sodium hydroxide solution was added, and the mixture was shear mixed for 10 seconds. The citric acid and caustic formed a weak buffer with a pH of 4.5. With the temperature maintained at 60° C., 1.508 grams of Diversa's Purifine™ (PLC lipase lot number 90BU002A1) and 0.1139 grams Novozymes' Lecitase® Ultra (PLA1 lipase lot number LYN05007) was added followed by 40 grams of de-ionized water and the entire mixture was shear mixed for 45 seconds. The oil mixture was agitated at normal speed for 30 minutes at a temperature of 60° C. The enzyme treated oil was then centrifuged; and the separated oil and wet gums were collected. The residual phosphorous in the PLC and PLA1 combined enzyme mixture at a pH of 4.5 produced a degummed oil with a residual phosphorous of 16.5 ppm.

Example 35

1999 grams of crude soybean oil containing 714.2 ppm of phosphorous was heated to 75-80° C. under normal agitation utilizing an overhead mixer. 2.0 grams of 50% w/w solution of citric acid was added and sheared for 1 minute. The oil underwent normal agitation for 1 hour with an overhead mixer. The oil was allowed to cool with agitation at normal speed until the oil temperature was 40° C., then 1.8 milliliters of 4 molar sodium hydroxide solution was added, and the mixture was shear mixed for 10 seconds. The citric acid and caustic formed a weak buffer with a pH of 4.5. With the temperature maintained at 40° C., 1.5010 grams of Diversa's Purifine™ (PLC lipase lot number 90BU002A1) and 0.1060 grams Novozymes' Lecitase® Ultra (PLA1 lipase lot number LYN05007) was added followed by 90 grams of de-ionized water and the entire mixture was shear mixed for 45 seconds. The oil mixture was agitated at normal speed for 120 minutes at a temperature of 40° C. The enzyme treated oil was then centrifuged; and the separated oil and wet gums were collected. The residual phosphorous in the PLC and PLA1 combined enzyme mixture at a pH of 4.5 produced a degummed oil with a residual phosphorous of 1.9 ppm.

Example 36

1999 grams of crude soybean oil containing 695.1 ppm of phosphorous was heated to 75-80° C. under normal agitation utilizing an overhead mixer. 2.0 grams of 50% w/w solution of citric acid was added and sheared for 1 minute. The oil underwent normal agitation for 1 hour with an overhead mixer. The oil was allowed to cool with agitation at normal speed until the oil temperature was 60° C., then 1.8 milliliters of 4 molar sodium hydroxide solution was added, and the mixture was shear mixed for 10 seconds. The citric acid and caustic formed a weak buffer with a pH of 4.5. With the temperature maintained at 60° C., 1.5296 grams of Diversa's Purifine™ (PLC lipase lot number 90BU002A1) and 0.1241 grams Novozymes' Lecitase® Ultra (PLA1 lipase lot number LYN05007) was added followed by 90 grams of de-ionized water and the entire mixture was shear mixed for 120 seconds. The oil mixture was agitated at normal speed for 30 minutes at a temperature of 60° C. The enzyme treated oil was then centrifuged; and the separated oil and wet gums were collected. The residual phosphorous in the PLC and PLA1 combined enzyme mixture at a pH of 4.5 produced a degummed oil with a residual phosphorous of 5.2 ppm.

Example 37

2005.2 grams of crude soybean oil containing 695.1 ppm of phosphorous was heated to 75-80° C. under normal agitation utilizing an overhead mixer. 2.0 grams of 50% w/w solution of citric acid was added and sheared for 1 minute. The oil underwent normal agitation for 1 hour with an overhead mixer. The oil was allowed to cool with agitation at normal speed until the oil temperature was 40° C. then 1.8 milliliters of 4 molar sodium hydroxide solution was added, and the mixture was shear mixed for 10 seconds. The citric acid and caustic formed a weak buffer with a pH of 4.5. With the temperature maintained at 40° C., 0.7422 grams of Diversa's Purifine™ (PLC lipase lot number 90BU002A1) and 0.1195 grams Novozymes' Lecitase® Ultra (PLA1 lipase lot number LYN05007) was added followed by 40 grams of de-ionized water and the entire mixture was shear mixed for 45 seconds. The oil mixture was agitated at normal speed for 30 minutes at a temperature of 40° C. The enzyme treated oil was then centrifuged; and the separated oil and wet gums were collected. The residual phosphorous in the PLC and PLA1 combined enzyme mixture at a pH of 4.5 produced a degummed oil with a residual phosphorous of 6.7 ppm.

Example 38

1998 grams of crude soybean oil containing 695.1 ppm of phosphorous was heated to 75-80° C. under normal agitation utilizing an overhead mixer. 2.0 grams of 50% w/w solution of citric acid was added and sheared for 1 minute. The oil underwent normal agitation for 1 hour with an overhead mixer. The oil was allowed to cool with agitation at normal speed until the oil temperature was 60° C., then 1.8 milliliters of 4 molar sodium hydroxide solution was added, and the mixture was shear mixed for 10 seconds. The citric acid and caustic formed a weak buffer with a pH of 4.5. With the temperature maintained at 60° C., 0.7429 grams of Diversa's Purifine™ (PLC lipase lot number 90BU002A1) and 0.1041 grams Novozymes' Lecitase® Ultra (PLA1 lipase lot number LYN05007) was added followed by 40 grams of de-ionized water and the entire mixture was shear mixed for 120 seconds. The oil mixture was agitated at normal speed for 120 minutes at a temperature of 60° C. The enzyme treated oil was then centrifuged; and the separated oil and wet gums were collected. The residual phosphorous in the PLC and PLA1 combined enzyme mixture at a pH of 4.5 produced a degummed oil with a residual phosphorous of 4.4 ppm.

TABLE 7

| Ex. | Enzyme Addition | PLC (ppm Active Enzyme) | PLA1 (ppm Active Enzyme) | Reaction Time (minutes) | Temp (C.) | pH | Water (%) | Agitation Time (seconds) | Phos (ppm) |
| --- | --- | --- | --- | --- | --- | --- | --- | --- | --- |
| 31 | Simultaneous | 20.9 | 0.7 | 120 | 40 | 4.5 | 2.0 | 120 | 10.7 |
| 32 | Simultaneous | 10.3 | 0.7 | 120 | 60 | 4.5 | 4.5 | 45 | 6.7 |
| 33 | Simultaneous | 10.4 | 0.7 | 30 | 40 | 4.5 | 4.5 | 120 | 2.2 |
| 34 | Simultaneous | 20.7 | 0.6 | 30 | 60 | 4.5 | 2.0 | 45 | 16.5 |
| 35 | Simultaneous | 20.7 | 0.6 | 120 | 40 | 4.5 | 4.5 | 45 | 1.9 |
| 36 | Simultaneous | 21.0 | 0.7 | 30 | 60 | 4.5 | 4.5 | 120 | 5.2 |
| 37 | Simultaneous | 10.2 | 0.6 | 30 | 40 | 4.5 | 2.0 | 45 | 6.7 |
| 38 | Simultaneous | 10.2 | 0.6 | 120 | 60 | 4.5 | 2.0 | 120 | 4.4 |

Figure 7:
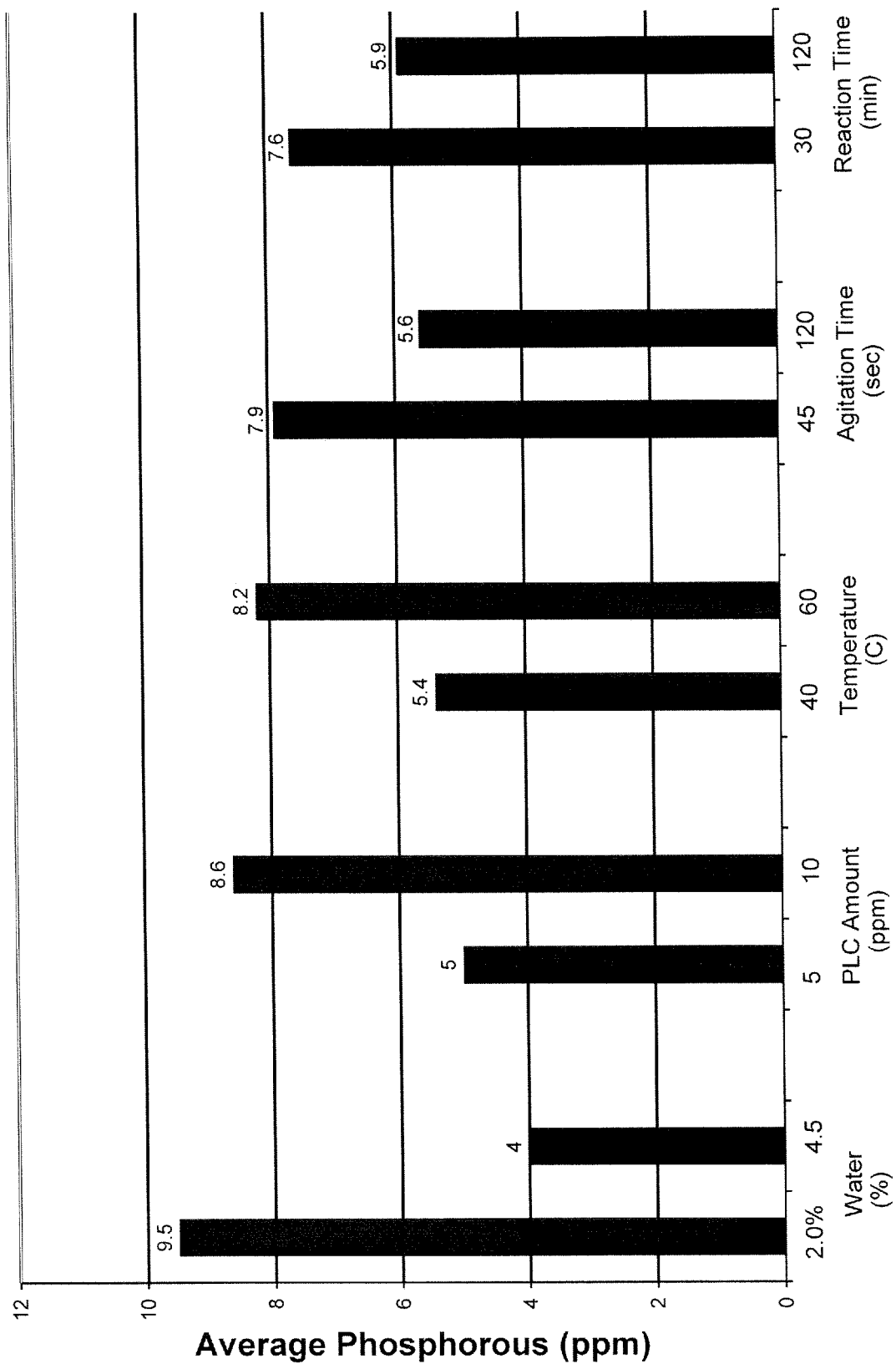
FIG. 7 is a graph summarizing the results of Examples 31-38, in which the average residual phosphorous in the degummed sample is plotted for each level of each experimental factor being evaluated.

FIG. 7 is a chart summarizing Examples 31-38, plotting the average final phosphorous amount at each level of each factor holding pH, PLA dosage, and combined addition constant.

The five factors evaluated in these Examples 31-38 are listed below in order of the magnitude of their effect on the degumming process. The effects are the differences in average phosphorus level (in absolute value) between the high and low factor settings.

Increased water dosage lowers the residual phosphorous
Decreased PLC dosage lowers the residual phosphorous
Decreased reaction temperature lowers the residual phosphorus
Increased agitation lowers the residual phosphorous
Increased reaction time lowers the residual phosphorous There has been disclosed a novel process for degumming of oils using a phospholipase A enzyme and a phospholipase C enzyme simultaneously. It has been found that, surprisingly, such a combination works better than either enzyme alone, even when by necessity one or the other of the enzymes is reacted under reaction conditions that are less than optimum for that enzyme. It also was a surprise to find that degumming at levels of less than about 10 ppm phosphorous, as low as about 5 ppm phosphorous, and even as low as about 3 ppm phosphorous in the final product could be achieved under the proper conditions with reaction times as low as about thirty minutes. Further, without wishing to be bound by theory, it appears that either the PLC enzyme or one of its hydrolysis reaction products is catalyzing the reaction of the PLA enzyme, allowing for the reaction time to be significantly less than the reaction time for either of the single enzymes.

Those skilled in the art will recognize from the foregoing disclosure that various operating parameters can be varied in the practice of the present invention, depending on the goals of a particular situation, while still remaining within the scope of the invention. For example, in determining the concentrations of the PLA and PLC enzymes to be used in a particular run, the choice will depend on whether the goal is to run at the lowest possible cost or the greatest possible performance. If the goal is to run at the lowest possible cost, then the concentration of PLA can be less than about 2.0 ppm, preferably less than about 1.0 ppm, and most preferably less than about 0.5 ppm. Such a low concentration of the PLA enzyme can still provide effective degumming in many situations. Conversely, if maximized performance is desired, the concentration of PLA is preferably at least about 0.5 ppm, more preferably at least about 1.0 ppm, and most preferably 2.0 ppm. Those skilled in the oil processing arts will understand how to vary the concentrations of the enzymes in the reaction mixture to obtain the desired balance of cost efficiency and product performance.

Variations in other processing conditions also are possible. The pH can be about 7.0, while pH of about 5.0 is preferable and pH of about 4.5 is presently preferred. The concentration of water in the system can be generally about 3.0%, and but can be as low as about 1.5% if reduced wastewater is desired, or as high as about 4.5% if greater degumming efficiency is desired. The reaction temperature can be as high as about 60° C., but is more preferably less than about 50° C., and surprisingly most preferable at about 40° C. The agitation time during initial mixing is can be about 45 seconds, is more preferably about 60 seconds, and is most preferably about 120 seconds. Finally, the duration of the enzyme reaction is advantageously less than about 60 minutes, and preferably about 30 minutes.

While preferred embodiments of the invention have been set forth herein, other embodiments encompassing the inventive method will be readily apparent to those skilled in the art, and all such embodiments and their equivalents are intended to be covered by this application and encompassed by the claims hereof.

We claim:

1. A method for degumming a soybean oil composition comprising
    (a) providing a soybean oil composition containing a quantity of phospholipids,
    (b) contacting said soybean oil composition simultaneously with one or more phospholipase A enzymes in a quantity of about 2 ppm of active enzyme or less and one or more phospholipase C enzymes in a quantity of about 30 ppm of active enzyme or less, under conditions sufficient for the enzymes to react with the phospholipids to create phospholipid reaction products, and
    (c) separating the phospholipid reaction products from the oil composition, the remaining oil composition after the separation being a degummed soybean oil composition, whereby during step (b) the reaction of said one or more phospholipase A enzymes proceeds at a faster rate than it would in the absence of said one or more phospholipase C enzymes, wherein the duration of the reaction of the enzymes with the phospholipids is less than one hour, and wherein said reaction of the enzymes with the phospholipids is conducted at a pH of about 3-7 at a temperature of about 40-80° C., and the degummed soybean oil composition of step (c) has a phospholipid content measured as parts per million of phosphorous of about 20 ppm or less.

2. The method of claim 1, wherein the duration of the reaction of the enzymes with the phospholipids is about thirty minutes.

3. The method of claim 1, wherein said one or more phospholipase A enzymes are selected from the group consisting of a phospholipase A1 enzyme and a phospholipase A2 enzyme.

4. The method of claim 1, wherein said one or more phospholipase C enzymes are selected from the group consisting of a phospholipase C enzyme and a phosphatidyl-inositol specific phospholipase C enzyme.

5. The method of claim 1, wherein said reaction of the enzymes with the phospholipids occurs at a temperature of about 40-60° C.

6. The method of claim 1, wherein said soybean oil composition comprises a crude soybean oil.

7. The method of claim 1, wherein said soybean oil composition comprises a previously degummed soybean oil.

8. The method of claim 1, wherein said PLC enzyme is present in a quantity of about 20 ppm of active enzyme or less.

9. The method of claim 8, wherein said PLC enzyme is present in a quantity of about 10 ppm of active enzyme or less.

10. The method of claim 1, wherein said PLA enzyme is present in a quantity of about 1 ppm of active enzyme or less.

11. The method of claim 10, wherein said PLA enzyme is present in a quantity of about 0.5 ppm of active enzyme or less.

12. The method of claim 1, wherein during step (b) the mixture of the soybean oil composition and the enzymes is initially shear mixed.

13. The method of claim 12, wherein said shear mixing continues for a duration of at least about 45 seconds.

14. The method of claim 1, wherein during step (b) a quantity of water is added.

15. The method of claim 14, wherein said quantity of water is at least about 1.5% by weight of the total mixture.

16. The method of claim 15, wherein said quantity of water is at least about 3.0% by weight of the total mixture.

17. The method of claim 16, wherein said quantity of water is at least about 4.5% by weight of the total mixture.

18. The method of claim 1, wherein said phospholipid content is about 10 ppm or less.

19. The method of claim 18, wherein said phospholipid content is about 5 ppm or less.

* * * * *